United States Patent
Al-Ali et al.

(10) Patent No.: US 9,392,945 B2
(45) Date of Patent: Jul. 19, 2016

(54) AUTOMATED CCHD SCREENING AND DETECTION

(71) Applicant: MASIMO CORPORATION, Irvine, CA (US)

(72) Inventors: Ammar Al-Ali, San Juan Capistrano, CA (US); Bilal Muhsin, San Clemente, CA (US)

(73) Assignee: Masimo Corporation, Irvine, CA (US)

( * ) Notice: Subject to any disclaimer, the term of this patent is extended or adjusted under 35 U.S.C. 154(b) by 552 days.

(21) Appl. No.: 13/733,782

(22) Filed: Jan. 3, 2013

(65) Prior Publication Data

US 2013/0190581 A1 Jul. 25, 2013

Related U.S. Application Data

(60) Provisional application No. 61/583,143, filed on Jan. 4, 2012, provisional application No. 61/703,132, filed on Sep. 19, 2012.

(51) Int. Cl.
*A61B 5/1455* (2006.01)
*A61B 5/02* (2006.01)

(52) U.S. Cl.
CPC ......... *A61B 5/02028* (2013.01); *A61B 5/14551* (2013.01)

(58) Field of Classification Search
CPC .............. A61B 5/1455; A61B 5/14551; A61B 5/14552; A61B 5/14532
USPC ......... 600/301, 309, 310, 322, 323, 331, 336, 600/473, 476; 356/41
See application file for complete search history.

(56) References Cited

U.S. PATENT DOCUMENTS

| | | | |
|---|---|---|---|
| 4,869,253 | A | 9/1989 | Craig et al. |
| 4,960,128 | A | 10/1990 | Gordon et al. |
| 4,964,408 | A | 10/1990 | Hink et al. |
| 5,041,187 | A | 8/1991 | Hink et al. |
| 5,069,213 | A | 12/1991 | Polczynski |
| 5,078,714 | A | 1/1992 | Katims |
| 5,163,438 | A | 11/1992 | Gordon et al. |
| 5,319,355 | A | 6/1994 | Russek |
| 5,337,744 | A | 8/1994 | Branigan |
| 5,341,805 | A | 8/1994 | Stavridi et al. |
| D353,195 | S | 12/1994 | Savage et al. |
| D353,196 | S | 12/1994 | Savage et al. |

(Continued)

OTHER PUBLICATIONS

PCT International Search Report and Written Opinion, dated Apr. 17, 2013, re: PCT Application No. PCT/US2013/020377, application dated Jan. 4, 2013, in 15 pages.

(Continued)

*Primary Examiner* — Tse Chen
*Assistant Examiner* — Chu Chuan Liu
(74) *Attorney, Agent, or Firm* — Knobbe, Martens, Olson & Bear LLP

(57) ABSTRACT

Automated critical congenital heart defect ("CCHD") screening systems and processes are described. A caregiver may be guided to use a single or dual sensor pulse oximeter to obtain pre- and post-ductal blood oxygenation measurements. A delta of the measurements indicates the possible existence or nonexistence of a CCHD. Errors in the measurements are reduced by a configurable measurement confidence threshold based on, for example, a perfusion index. Measurement data may be stored and retrieved from a remote data processing center for repeated screenings.

14 Claims, 16 Drawing Sheets

(56) References Cited

U.S. PATENT DOCUMENTS

| | | | |
|---|---|---|---|
| 5,377,676 A | 1/1995 | Vari et al. |
| D359,546 S | 6/1995 | Savage et al. |
| 5,431,170 A | 7/1995 | Mathews |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,083,172 A | 7/2000 | Baker, Jr. et al. |
| 6,088,607 A | 7/2000 | Diab et al. |
| 6,110,522 A | 8/2000 | Lepper, Jr. et al. |
| 6,124,597 A | 9/2000 | Shehada |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,301,493 B1 | 10/2001 | Marro et al. |
| 6,317,627 B1 | 11/2001 | Ennen et al. |
| 6,321,100 B1 | 11/2001 | Parker |
| 6,321,110 B1 * | 11/2001 | Ito ............................ G06F 3/015 356/41 |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kianl et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |

(56) References Cited

U.S. PATENT DOCUMENTS

| | | |
|---|---|---|
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali et al. |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali et al. |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty et al. |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,942,824 B1 | 5/2011 | Kayyali et al. |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Al-Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,224,411 B2 | 7/2012 | Al-Ali et al. |
| 8,228,181 B2 | 7/2012 | Al-Ali |

(56) References Cited

U.S. PATENT DOCUMENTS

| | | |
|---|---|---|
| 8,229,533 B2 | 7/2012 | Diab et al. |
| 8,255,026 B1 | 8/2012 | Al-Ali |
| 8,255,028 B2 | 8/2012 | Al-Ali et al. |
| 8,260,577 B2 | 9/2012 | Weber et al. |
| 8,274,360 B2 | 9/2012 | Sampath et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,457,707 B2 | 6/2013 | Kiani |
| 2004/0034293 A1* | 2/2004 | Kimball ............ A61B 5/14551 600/323 |
| 2004/0097797 A1 | 5/2004 | Porges et al. |
| 2008/0009754 A1 | 1/2008 | Chang |
| 2008/0071155 A1 | 3/2008 | Kiani |
| 2008/0221464 A1 | 9/2008 | Al-Ali |
| 2013/0331670 A1 | 12/2013 | Kiani |

OTHER PUBLICATIONS

PCT Preliminary Report of Patentability, dated Jul. 17, 2014, for application No. PCT/US2013/020377 in 9 pages.

Hoke et al., "Oxygen saturation as a screening test for critical congenital heart disease: a preliminary study", Pediatr Cardiol 23:403-409, 2002.

* cited by examiner

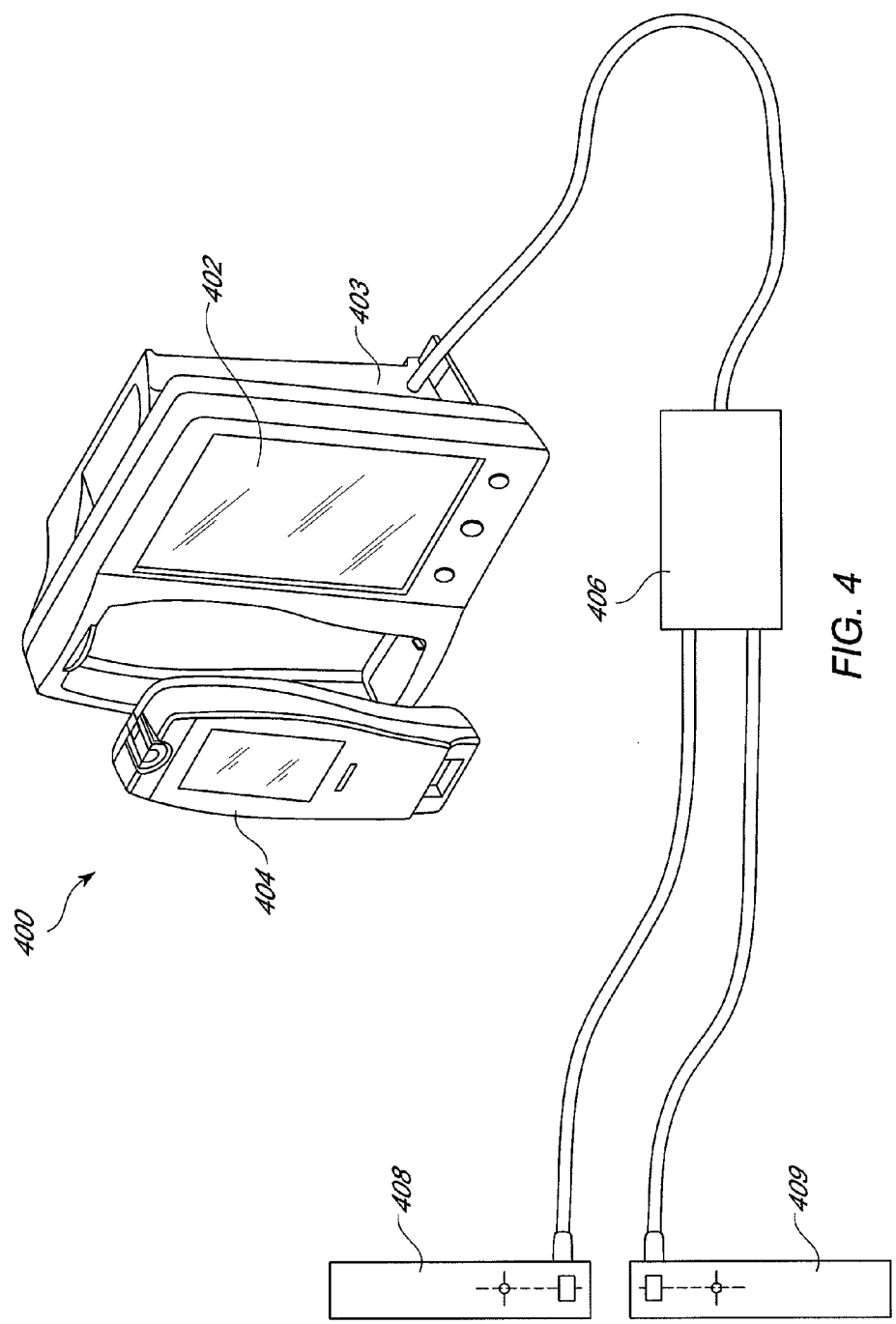

Step 1: Pre-Ductal Instruction

Step 2: Pre-Ductal Instruction

Step 2: Sensor Error

Step 3: Post-Ductal Instruction

Step 4: Post-Ductal Measure

Step 4: Sensor Error

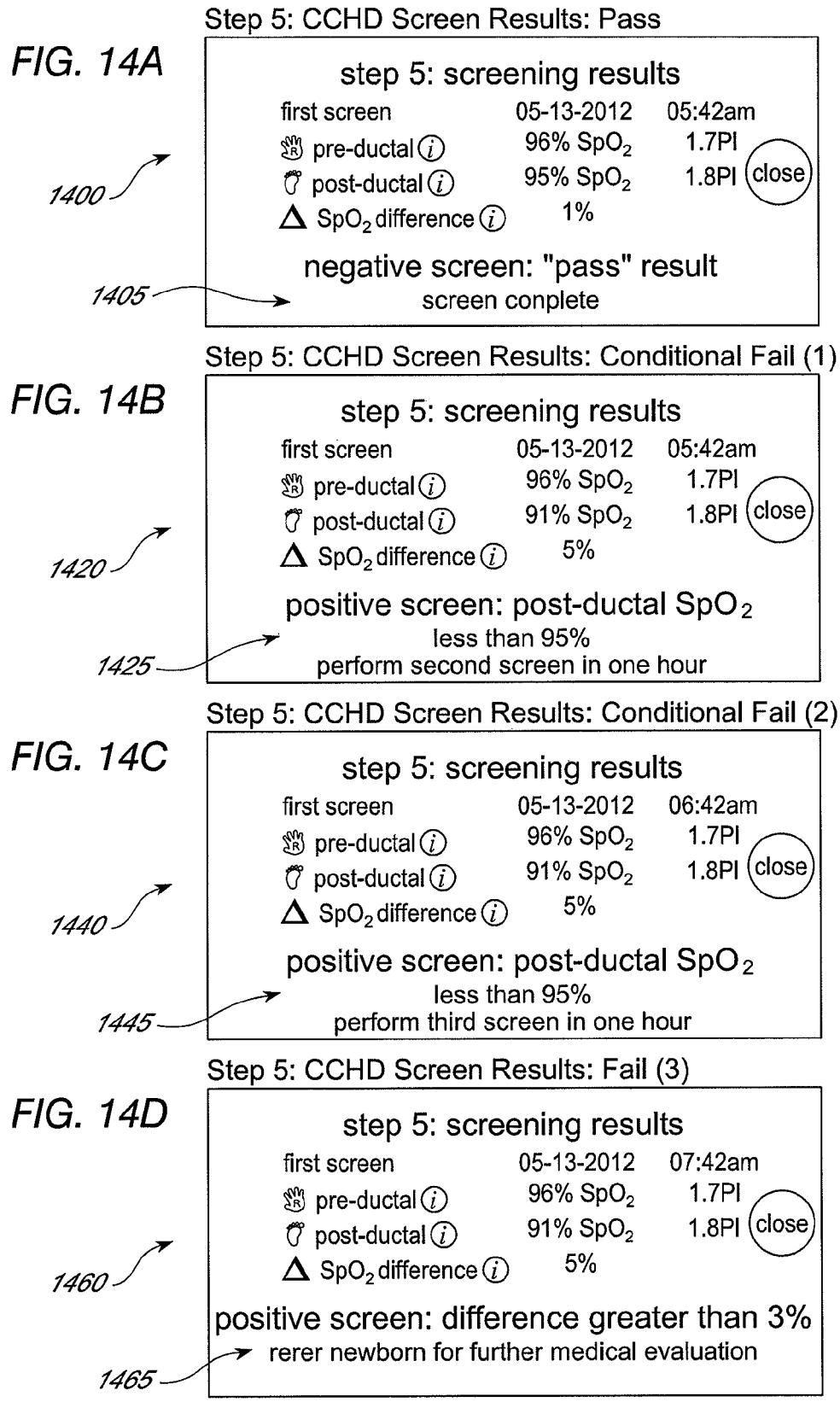

AUTOMATED CCHD SCREENING AND DETECTION

PRIORITY CLAIM AND RELATED APPLICATIONS

This application claims a priority benefit under 35 U.S.C. §119 to the following U.S. Provisional Patent Applications:

| Ser. No. | Date | Title |
| --- | --- | --- |
| 61/583,143, | Jan. 4, 2012, | SYSTEMS AND METHODS AUTOMATING CCHD SCREENING AND DETECTION, |
| 61/703,132, | Sep. 19, 2012, | SYSTEMS AND METHODS AUTOMATING CCHD SCREENING AND DETECTION. |

Each of the foregoing disclosures is incorporated by reference herein in its entirety.

FIELD OF THE DISCLOSURE

The present application relates to the field of pulse oximetry. Specifically, the present application relates to the field of infant oxygen saturation monitoring and congenital heart defects screening.

BACKGROUND OF THE DISCLOSURE

Pulse oximetry screening can identify some critical congenital heart defects ("CCHDs"), which also are known collectively in some instances as critical congenital heart disease. CCHDs are structural heart defects that often are associated with hypoxia among infants during the newborn period. Infants with CCHDs are at risk for significant morbidity or mortality. There are several defects that could be considered CCHDs. However, in the context of newborn pulse oximetry screening at the time of preparation of the present application, the Centers for Disease Control and Prevention ("CDC") for the U.S. government classify seven (7) defects as CCHD: hypoplastic left heart syndrome, pulmonary atresia (with intact septum), tetralogy of Fallot, total anomalous pulmonary venous return, transposition of the great arteries, tricuspid atresia, and truncus arteriosus. According to the CDC, these seven CCHDs represent about seventeen to about thirty one percent (17-31%) of all congenital heart disease.

Patent ductus arteriosus ("PDA") is common in infants with several or more of the above seven (7) defects. In the developing fetus, the ductus arteriosus ("DA") 102 shown in FIG. 1 is the vascular connection between the pulmonary artery 106 and the aortic arch 104 that allows most of the blood from the right ventricle 110 to bypass the fetus' fluid-filled compressed lungs. During fetal development, this shunt protects the right ventricle 110 from pumping against the high resistance in the lungs 108, which can lead to right ventricular failure if the DA 102 closes in-utero.

When the newborn takes its first breath, the lungs open and pulmonary vascular resistance decreases. In normal newborns, the DA is substantially closed within twelve to twenty four (12-24) hours after birth, and is completely sealed after three (3) weeks.

In the case of PDA, high pressure oxygenated blood from the aorta 104 leaks or flows back into the pulmonary artery 112 and back to the lungs 108 with normal deoxygenated venous blood. The additional fluid returning to the lungs increases lung pressure to the point that the infant may have greater difficulty inflating the lungs. This uses more calories than normal and often interferes with feeding in infancy. Moreover, an open (patent) DA 102 alters the flow in the descending aorta 118, which, as a result, changes the blood oxygen saturation in the feet.

Without screening, some newborns with CCHDs might be missed because the signs of CCHD might not be evident before an infant is discharged from the hospital after birth. Other heart defects might be considered secondary screening targets. Some of these heart defects can be just as severe as the primary screening targets and also require intervention soon after birth. These secondary targets include aortic arch atresia or hypoplasia, interrupted aortic arch, coarctation of the aorta, double-outlet right ventricle, Ebstein anomaly, pulmonary stenosis, atrioventricular septal defect, ventricular septal defect, and single ventricle defects (other than hypoplastic left heart syndrome and tricuspid atresia).

Current CDC recommendations focus on screening infants in the well-baby nursery and in intermediate care nurseries or other units in which discharge from the hospital is common during an infant's first week of life. At the time of preparation of the present application, the CDC promulgated a CCHD screening process 200 reproduced as FIG. 2, directed toward oxygen saturation measurements, or percentages measured using, for example, a standard pulse oximeter.

According to the CDC's CCHD screening process 200 of FIG. 2, a screen is considered positive (see box 228) if (1) any oxygen saturation measurement is less than ninety percent (<90%) (in the initial screen or in repeat screens) (see boxes 206, 214, and 222); (2) the oxygen saturation measurement is less than ninety five percent (<95%) in the right hand and foot on three measures (see boxes 208, 216, and 224), each separated by one (1) hour (see boxes 204, 212, 220); or (3) a greater than three percent (>3%) absolute difference exists in oxygen saturation measurements between the right hand and foot on three measures (see boxes 208, 216, and 224), each separated by one (1) hour. Any screening that is greater than or equal to ninety five percent (≥95%) in the right hand or foot with a less than or equal to three percent (≤3%) absolute difference in oxygen saturation measurements between the right hand and foot is considered a negative screen and screening would end (see boxes 210, 218, 226, and 230).

The CDC recommends any infant receiving a positive screen receive a diagnostic echocardiogram, which would involve an echocardiogram within the hospital or birthing center, transport to another institution for the procedure, or use of telemedicine for remote evaluation. This can be expensive, disruptive, and possibly harmful to the infant. For example, at the time of preparation of the present application, an echocardiogram to verify an out-of-range (positive) screen could cost several hundred dollars.

Thus, false positives are to be avoided. The CDC believes that false positives are decreased if the infant is alert, and timing pulse oximetry screening around the time of newborn hearing screening improves efficiency.

Pulse oximetry screening may not detect all CCHDs, so it is possible for a baby with a negative screening result to still have a CCHD or other congenital heart defect.

SUMMARY OF THE DISCLOSURE

The CCHD screening process of FIG. 2 incorporates multiple measurement sites, such as, for example, a baseline site of the right hand and a secondary site of the feet or left hand. In some cases, a stereo pulse oximeter, such as the one disclosed in U.S. Pat. No. 6,334,065 (the '065 patent), incorporated by reference herein, could use two (2) or more of its associated sensors, one for each of multiple sites to accomplish the measurements. In fact, the '065 patent discusses the use of its sensor for multiple sites to determine indications of PDA, Persistent Pulmonary Hypertension in Neonates ("PPHN"), and Aortic Coarctation. However, very few if any institutions possess stereo pulse oximeters.

Rather, in most if not all circumstances, the CCHD screening process of FIG. 2 will be implemented on a single site pulse oximeter. The caregiver will apply the sensor to the first site, such as the baseline right hand, and take measurements. The caregiver will then remove the sensor from the first site, and transfer it to the second site, such as a foot, left hand, etc. and take measurements. As shown in FIG. 2, the CCHD screening process relies on the delta (or difference) between the two measurements.

Drawbacks may occur using the single sensor implementation. For example, there will be a time differential between the first baseline measurement and the second alternate site measurement when the caregiver changes sites. In infants, the parameters measureable with today's oximeters, including but not limited to oxygen saturation ("$SpO_2$"), vary within relatively short periods. This is exacerbated when infants are exited, crying, or otherwise agitated.

In the most straightforward scenario where the $SpO_2$ measurements are somewhat varying, the single sensor implementation of CCHD screening may determine, for example, an infant's $SpO_2$ during a valley or trough of varying $SpO_2$ values for the baseline measurement, and quite accidentally during a peak of varying $SpO_2$ values for the alternate measurement. Such time displaced measurements could appear anywhere on an infant's $SpO_2$ waveform. Thus, the differential between the baseline measurement and the alternate measurement, which is the key to determining positive or negative screenings under the CCHD screening process, could be subject to error. This is exacerbated as the CCHD screening process may require three (3) or more screenings before rendering a conclusion. Thus, a screening process may include measurements taken under different data conditions at each screen, and then again across the screens.

To overcome these and other drawbacks, the present disclosure includes systems and methods automating CCHD screening and detection. In an embodiment, a processor executes one or more processing modules to improve a likelihood that during a single sensor implementation of CCHD screening, the measurement values while time displaced, correspond to data conditions similar to one another. In addition, the processing module may determine the best sites for measurements.

In an embodiment, an oximeter or communicating monitor controls and tracks the implementation of the screening process, including instructions to caregivers on next steps. For example, a straightforward instruction may include "Attach Sensor to Right Hand," "Attach Sensor to Alternate Site," "Attach Sensor to Right Foot," "Attach Sensor to Left Foot," "Calm Patient," "Adjust Sensor Positioning," or the like. The oximeter may also include a quality indicator providing information on the confidence in the screening measurements. A quality measure may be included for each measurement, for the entire screen, or the like. For example, the display may indicate "Positive Screen, 72% Confidence." In an embodiment, a minimum confidence threshold may be used to instruct a caregiver to repeat the measurements and/or restart the screening process. Moreover, the oximeter may produce an audio/visual alarm indicating time for a repeat screen, may accept patient information including a patient identifier, and the like.

In other embodiments, the oximeter may communicate with a host digital network or system to store or upload measurement data associated with a unique identifier to a remote processing center. That network or system may include multiple networks or systems. However, the oximeter may access previously stored information, such as, for example, earlier screening data stored at the remote network, to complete or increment the CCHD screening process. In an embodiment, a first network may be an institutional network such as a hospital data system, a cellular or other data system, or the like, wirelessly communicating with the oximeter or monitor. The system or systems eventually allow communication to a remote data server or processing center that stores the measurement information in a manner that provides for retrieval and appropriate association with newly acquired data.

For purposes of summarizing the disclosure, certain aspects, advantages and novel features thereof have been described herein. Of course, it is to be understood that not necessarily all such aspects, advantages or features will be embodied in any particular embodiment of the invention.

BRIEF DESCRIPTION OF THE DRAWINGS

The following drawings and the associated descriptions are provided to illustrate embodiments of the present disclosure and do not limit the scope of the claims.

FIG. 4 illustrates a simplified perspective view and block diagram of a pulse oximeter configured to perform a CCHD screen process including dual sensors, according to an embodiment of present disclosure.

FIGS. 12A-C, 13A-C, and 14A-D illustrate example screen shots, including instructions for single sensor operation, of a pulse oximeter monitor configured for measuring CCHD, according to an embodiment of the present disclosure.

DETAILED DESCRIPTION

Figure 2:
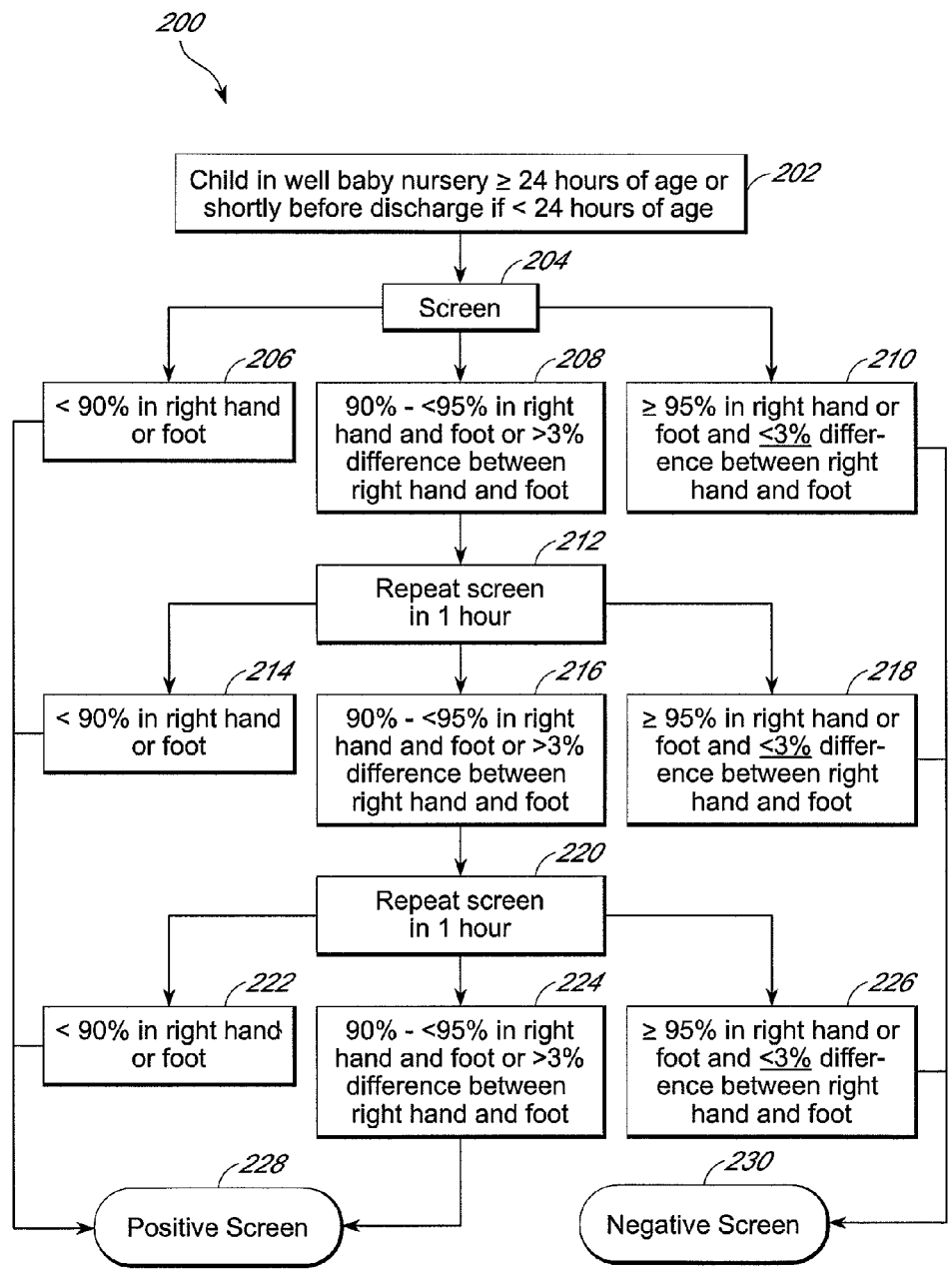
FIG. 2 illustrates an embodiment of a CCHD screening process provided by the CDC.

The present disclosure generally relates to systems and methods automating critical congenital heart defects ("CCHDs") screening and detection. In an embodiment, the CCHD screening process may be implemented on a single site pulse oximeter. A caregiver will apply the pulse oximeter sensor to the first site, such as the right hand, and take baseline measurements including, for example, blood oxygen saturation ("$SpO_2$"). The caregiver will then remove the pulse oximeter sensor from the first site, and transfer it to the second site, such as, for example, a foot or left hand, and take measurements. As shown in FIG. 2, and as described above, the CCHD screening process relies on the delta (or difference) between the two measurements. Then, a processor executes one or more processing modules to improve a likelihood that during a single sensor implementation of CCHD screening, the measurement values, while time displaced, correspond to data conditions similar to one another. In addition, the processing module may determine the best sites for measurements.

As used herein, the terms pulse oximeter, CCHD screening system, CCHD measurement device, and CCHD monitor may be used interchangeably.

Figure 1:
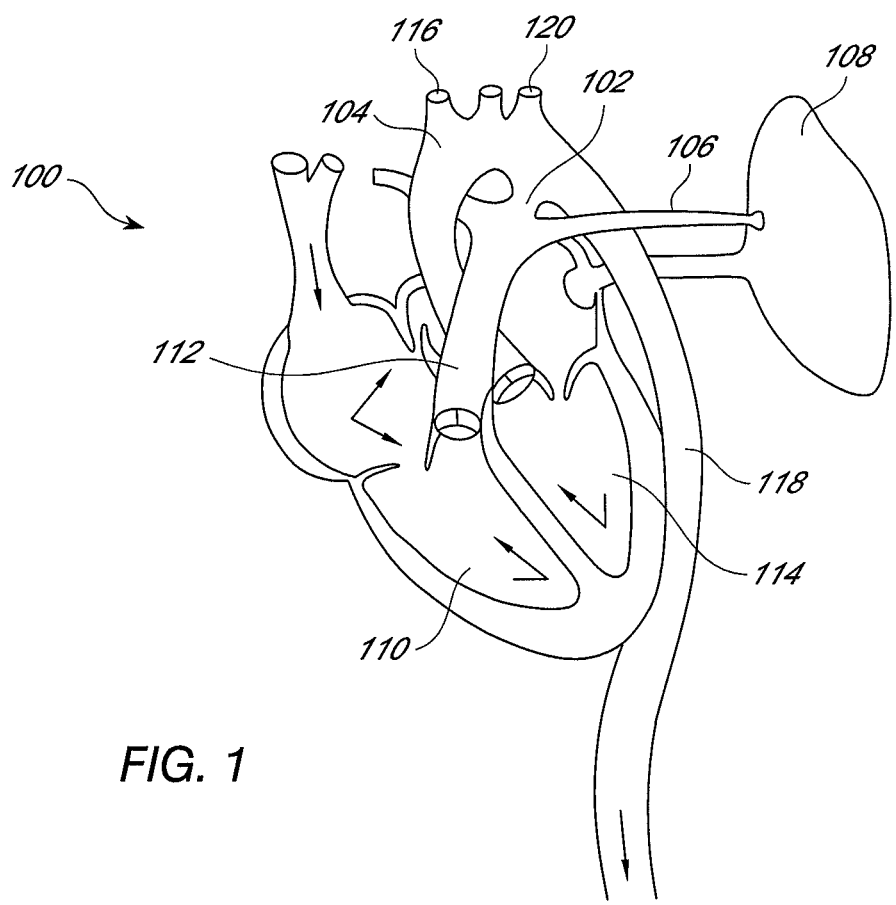
FIG. 1 illustrates a diagram of a portion of a circulatory system including a heart having a patent or open ductus arteriosus.

FIG. 1 illustrates an infant heart 100 having patent ductus arteriosus ("PDA"), and lungs 108. The infant heart 100 includes a ductus arteriosus 102, an aorta 104, a pulmonary artery 106, a right ventricle 110, a main pulmonary artery 112, a left ventricle 114, an innominate artery 116, a descending aorta 118, and a subclavian artery 120. The ductus arteriosus 102 frequently fails to close in premature infants, allowing left-to-right shunting, i.e. oxygenated "red" blood flows from the aorta 104 to the now unconstricted pulmonary artery 106 and recirculates through the lungs 108. A persistent patent results in pulmonary hyperperfusion and an enlarged right ventricle 110, which leads to a variety of abnormal respiratory, cardiac and genitourinary symptoms. Current PDA diagnosis involves physical examination, chest x-ray, blood gas analysis, echocardiogram, or a combination of the above. For example, large PDAs may be associated with a soft, long, low-frequency murmur detectable with a stethoscope. As another example, two-dimensional, color Doppler echocardiography may show a retrograde flow from the ductus arteriosus 102 into the main pulmonary artery 112. Once a problematic PDA is detected, closure can be effected medically with indomethacin or ibuprofen or surgically by ligation. Multiple doses of indomethacin are commonplace but can still result in patency, demanding ligation. A drawback to current diagnostic techniques is that clinical symptoms of a PDA can vary on an hourly basis, requiring extended and inherently intermittent testing.

In a single sensor implementation of noninvasive PDA determination or CCHD screen (as described below in referenced to FIGS. 3A-C), a sensor, such as a blood oxygenation sensor, may be placed on the right hand to determine a baseline of physiological data. For example, a pulse oximetry sensor at the right hand provides physiological data signals indicative of arterial oxygen saturation and a plethysmograph for blood circulating from the left ventricle 114 through the innominate artery 116, which supplies the right subclavian artery leading to the right arm. Because the innominate artery 116 is upstream from the PDA shunt at the ductus arteriosus 102, the oxygen saturation value and plethysmograph waveform obtained from the right hand are relatively unaffected by the shunt and serve as a baseline for comparison with readings from other tissue sites.

A sensor may then be placed on a foot to provide oxygen status for blood supplied from the descending aorta 118. The shunt at the ductus arteriosus 102 affects aortic flow. In particular, the shunt allows a transitory left-to-right flow during systole from the high pressure aorta 104 to the low pressure pulmonary artery 106 circulation. This left-to-right flow through the shunt at the ductus arteriosus 102 alters the flow in the descending aorta 118 and, as a result, affects the oxygen saturation value and plethysmograph waveform measured at the foot. The PDA condition, therefore, may be manifested as a normal plethysmograph with a characteristically narrow peak and well-defined dicrotic notch at the right-hand baseline site compared with a damped plethysmograph with a broadened peak and reduced or missing notch at the foot site. Further, the foot site waveform may be phase shifted from the baseline waveform. These plethysmograph differences are accompanied by comparable differences in arterial oxygen saturation values between the right-hand site and the foot site.

As an alternative, the sensor may be placed on the left hand to provide oxygen status for blood circulating from the left ventricle through the left subclavian artery 120 that supplies the left arm. Because the left subclavian artery 120 is nearer the shunt at the ductus arteriosus 102 than the further upstream innominate artery 116, it may experience some alteration in flow due to the shunt at the ductus arteriosus 102. The PDA condition, therefore, may also be manifested as an altered plethysmograph waveform at a left hand site as compared with the right hand baseline site, although likely to a lesser degree than with a foot site. Thus, the PDA condition, and thus a CCHD condition, can be detected and its treatment monitored from a delta in saturation (i.e., difference in $SpO_2$) values and plethysmograph morphology and phase comparisons between a right hand baseline sensor site and one or more other sites, such as the left hand or foot. One of ordinary skill will recognize that multiple site comparisons using an oximeter may also be used to detect other cardiac abnormalities that cause mixing of oxygenated and deoxygenated blood, such as a ventricular hole or a patent foramen. Further, abnormal mixing of oxygenated and deoxygenated blood may also be manifested in physiological data measurements other than oxygen saturation provided by an advanced patient monitor or pulse oximeter.

Figure 3A:
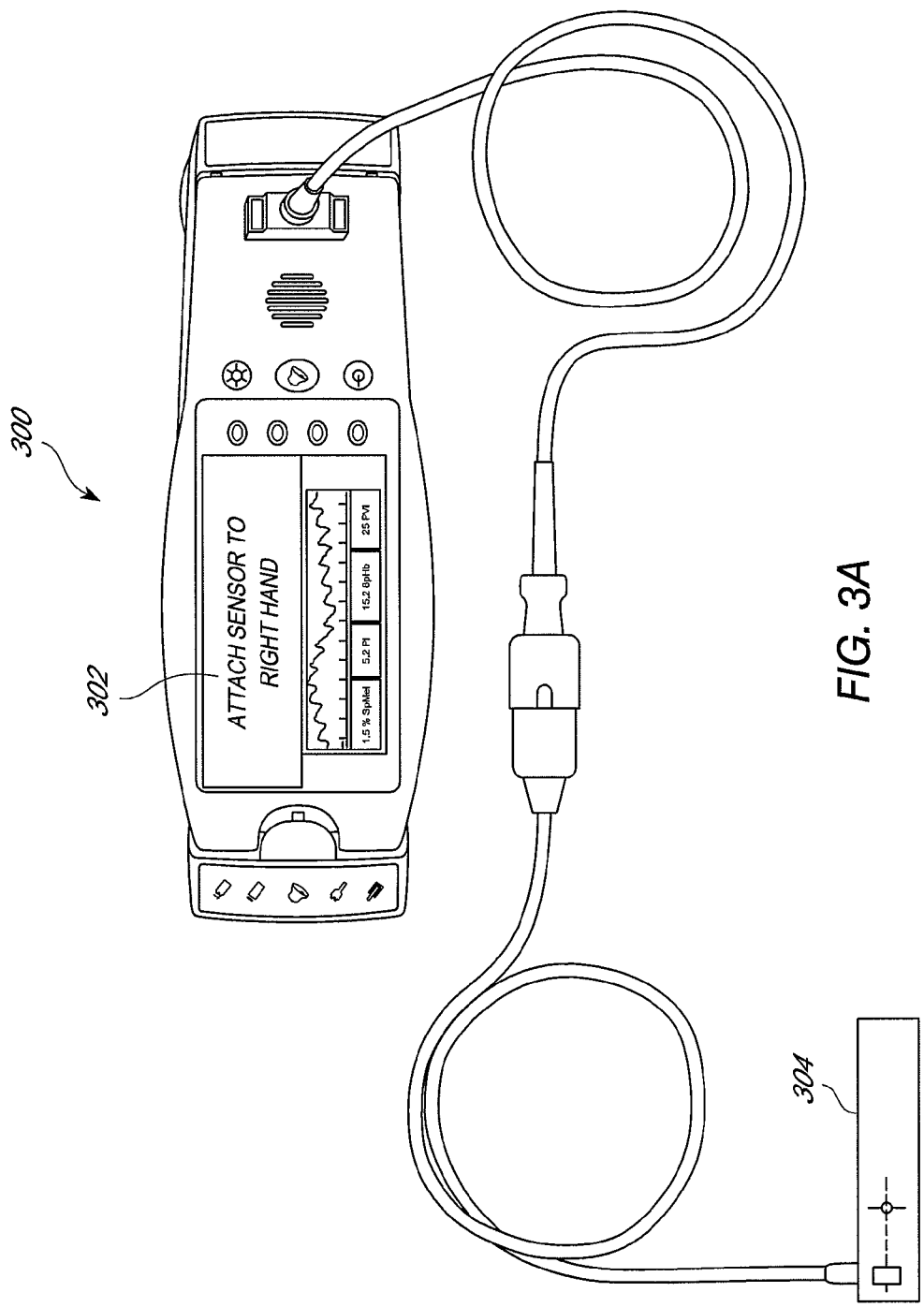
FIG. 3A illustrates a simplified view of a pulse oximeter configured to perform a CCHD screening process, according to an embodiment of the disclosure.

FIG. 3A illustrates a simplified view of a pulse oximeter configured to perform a CCHD screening process with a single sensor (as described above), according to an embodiment of the disclosure. FIG. 3A includes a pulse oximeter 300, a display 302, and a sensor 304. In an embodiment, the sensor 304 may be noninvasively attached to the patient's finger. The sensor 304 may measure various blood analytes noninvasively using multi-stream spectroscopy. In an embodiment, the multi-stream spectroscopy may employ visible, infrared and near infrared wavelengths. The sensor 304 may be capable of noninvasively measuring blood analytes or percentages thereof (e.g., saturation) based on various combinations of features and components.

The sensor 304 may include photocommunicative components, such as an emitter, a detector, and other components. The emitter may include a plurality of sets of optical sources that, in an embodiment, are arranged together as a point source. The various optical sources may emit a sequence of optical radiation pulses at different wavelengths towards a measurement site, such as a patient's finger. Detectors may then detect optical radiation from the measurement site. The optical sources and optical radiation detectors may operate at any appropriate wavelength, including infrared, near infrared, visible light, and ultraviolet. In addition, the optical sources and optical radiation detectors may operate at any appropriate wavelength, and such modifications to the embodiments desirable to operate at any such wavelength will be apparent to those skilled in the art. In some embodiments, the sensor 304 may be any of a disposable, reusable, and/or resposable sensor. Generally, for CCHD measurements, a sensor configured for use with an infant is desirable. In some embodiments, this may include a finger, toe, or ear sensor. In an embodiment, the sensor 304 may also be a wrist-type sensor configured to surround the wrist or ankle of an infant.

The sensor 304 is coupled to the pulse oximeter 300 that processes and/or displays the sensor 304's output, on, for example, display 302. The sensor 304 may additionally be coupled to one or more monitors that process and/or display the sensor 304's output. As described below in reference to FIG. 3B, the pulse oximeter 300 may include various components, such as a sensor front end, a signal processor, and/or a display, among other things.

The sensor 304 may be integrated with a monitor (such as the pulse oximeter 300), for example, into a handheld unit including the sensor 304, a display and user controls. In other embodiments, the sensor 304 may communicate with one or more processing devices. The communication may be through wire(s), cable(s), flex circuit(s), wireless technologies, or other suitable analog or digital communication methodologies and devices to perform those methodologies. Many of the foregoing arrangements allow the sensor 304 to be attached to the measurement site while the device (such as the pulse oximeter 300) is attached elsewhere on a patient, such as the patient's arm, or placed at a location near the patient, such as a bed, shelf or table. The sensor 304 and/or pulse oximeter 300 may also provide outputs to a storage device or network interface.

Figure 3B:
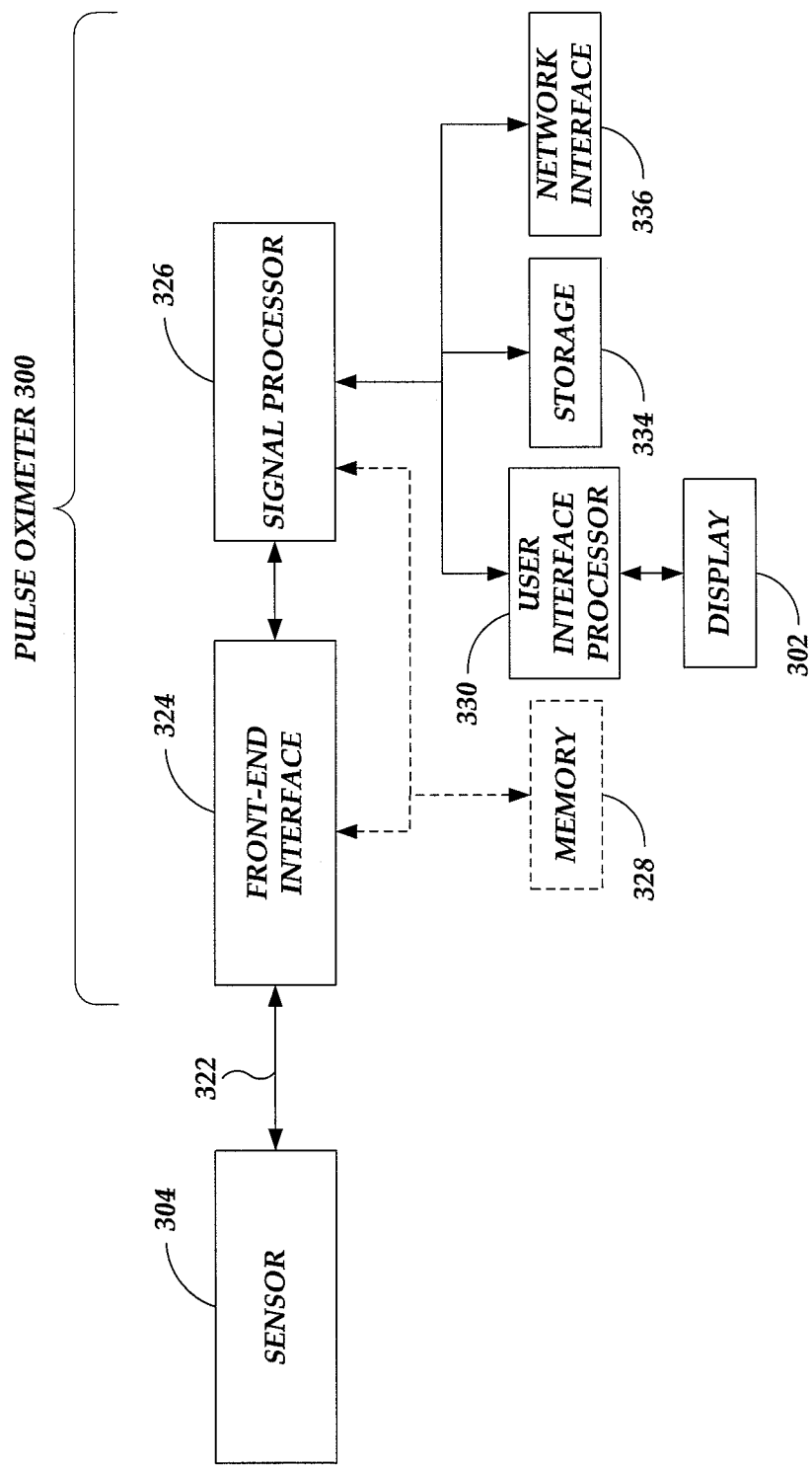
FIG. 3B illustrates a simplified block diagram of a pulse oximeter configured to perform a CCHD screening process, according to an embodiment of the disclosure.

FIG. 3B illustrates a simplified block diagram of a pulse oximeter configured to perform a CCHD screening process, as described above with reference to FIG. 3A. FIG. 3B includes the pulse oximeter 300, the sensor 304, and a communications link 322. The pulse oximeter 300 includes a front-end interface 324, a signal processor 326, a user interface processor 330, the display 302, a storage 334, a network interface 336, and an optional memory 328. In an embodiment, the signal processor 326 includes processing logic that determines measurements, for example, $SpO_2$ and/or PI. The signal processor 326 may be implemented using one or more microprocessors or subprocessors (e.g., cores), digital signal processors, application specific integrated circuits (ASICs), field programmable gate arrays (FPGAs), combinations of the same, and the like.

The signal processor 326 may provide various signals through the front-end interface 324 and the communications link 322 that control the operation of the sensor 304. For example, the signal processor 326 may provide an emitter control signal to the sensor 304. Additionally, measurement data may be transmitted from the sensor 304 to the signal processor 326. As also shown, the optional memory 328 may be included in the front-end interface 324 and/or in the signal processor 326. This optional memory 328 may serve as a buffer or storage location for the front-end interface 324 and/or the signal processor 326, among other uses.

The user interface processor 330 may provide an output, for example, on the display 302, for presentation to a user of the pulse oximeter 300. The user interface processor 330 and/or the display 302 may be implemented as a touch-screen display, an LCD display, an organic LED display, or the like. In addition, the user interface processor 330 and/or display 302 may include a flip screen, a screen that can be moved from one side to another on the pulse oximeter 300, or may include an ability to reorient its display indicia responsive to user input or device orientation. In alternative embodiments, the pulse oximeter 300 may be provided without the display 302 and may simply provide an output signal to a separate display or system.

The storage 334 and the network interface 336 represent other optional output connections that can be included in the pulse oximeter 300. The storage 334 may include any computer-readable medium, such as a memory device, hard disk storage, EEPROM, flash drive, or the like. Various software and/or firmware applications can be stored in the storage 334, which may be executed by the signal processor 326 and/or another processor of the pulse oximeter 300. The network interface 336 may be a serial bus port (RS-232/RS-485), a Universal Serial Bus (USB) port, an Ethernet port, a wireless interface (e.g., WiFi such as any 802.1x interface, including an internal wireless card), or other suitable communication device(s) that allows the pulse oximeter 300 to communicate and share data with other devices (such as, for example, a remote data processing center as described below in reference to FIG. 5). The pulse oximeter 300 may also include various other components not shown, such as a microprocessor, graphics processor, and/or controller to output a user interface, to control data communications, to compute data trending, and/or to perform other operations.

Although not shown in the depicted embodiment, the pulse oximeter 300 may include various other components or may be configured in different ways. For example, the sensor 304 may measure additional advanced parameters. As described below, the pulse oximeter 300 may prompt the user to take specific actions through the display 302 to, for example, accomplish the CCHD screening process.

Figure 3C:
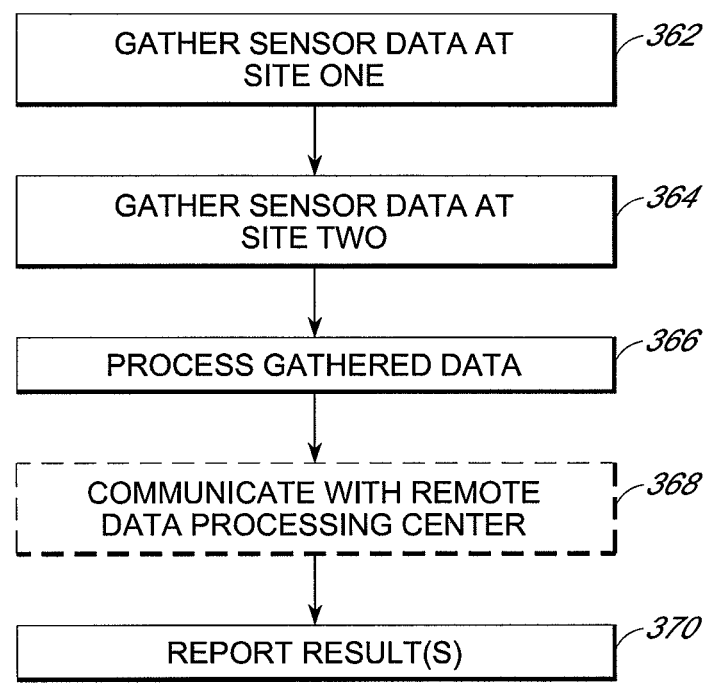
FIG. 3C illustrates an example CCHD screening process according to an embodiment of the present disclosure.

FIG. 3C illustrates an example CCHD screening process according to an embodiment of the present disclosure. This CCHD screening process may be accomplished with, for example, the pulse oximeter 300 of FIGS. 3A and 3B. At box 362, sensor data is gathered at a first site. For example, at this point the user/caregiver may be instructed to attach the pulse oximeter sensor (for example, the sensor 304) to the patient's right hand for a pre-ductal measurement. At box 364, sensor data is gathered at a second site. For example, at this point the user/caregiver may be instructed to attach the pulse oximeter sensor (for example, the sensor 304) to the patient's foot or left hand for a post-ductal measurement. In each of boxes 362 and 364, the measurement data may be transmitted from the sensor 304, through the communications link 322 and front-end interface 324, to the signal processor 326.

At box 366, the gathered pre- and post-ductal measurement data is processed by, for example, the signal processor 326. The gathered data is processed to provide both screening results (for example, the pre- and post-ductal $SpO_2$ measurements and the delta between the two), but also to reduce errors in the measurements. As stated above, drawbacks arise when data from each time-displaced measurement (baseline and alternate, pre- and post-ductal) is not carefully selected. For example, normal infant $SpO_2$ values may drift up and down more than two percent (2%). If a baby holds its breath during onset of crying, values may drift more than twenty percent (20%) in a very short time. If by chance the baseline was taken at a coincidental peak in normal variation, and the alternate was taken during crying or even at a valley or trough of normal variation, such error may impact a CCHD screening process, which, as shown in FIG. 2, may change the result based on a three percent (3%) differential between baseline and alternate.

As described above, FIG. 2 depicts the Centers for Disease Control and Prevention's ("CDC's") recommended CCHD screening process 200. A screen is considered positive (see box 228) if (1) any oxygen saturation measurement is less than ninety percent (<90%) (in the initial screen or in repeat screens) (see boxes 206, 214, and 222); (2) the oxygen saturation measurement is less than ninety five percent (<95%) in the right hand and foot on three measures (see boxes 208, 216, and 224), each separated by one (1) hour (see boxes 204, 212, 220); or (3) a greater than three percent (>3%) absolute difference exists in oxygen saturation measurements between the right hand and foot on three measures (see boxes 208, 216, and 224), each separated by one (1) hour. Any screening that is greater than or equal to ninety five percent (≥95%) in the right hand or foot with a less than or equal to three percent (≤3%) absolute difference in oxygen saturation measurements between the right hand and foot is considered a negative screen and screening would end (see boxes 210, 218, 226, and 230).

Figure 16:
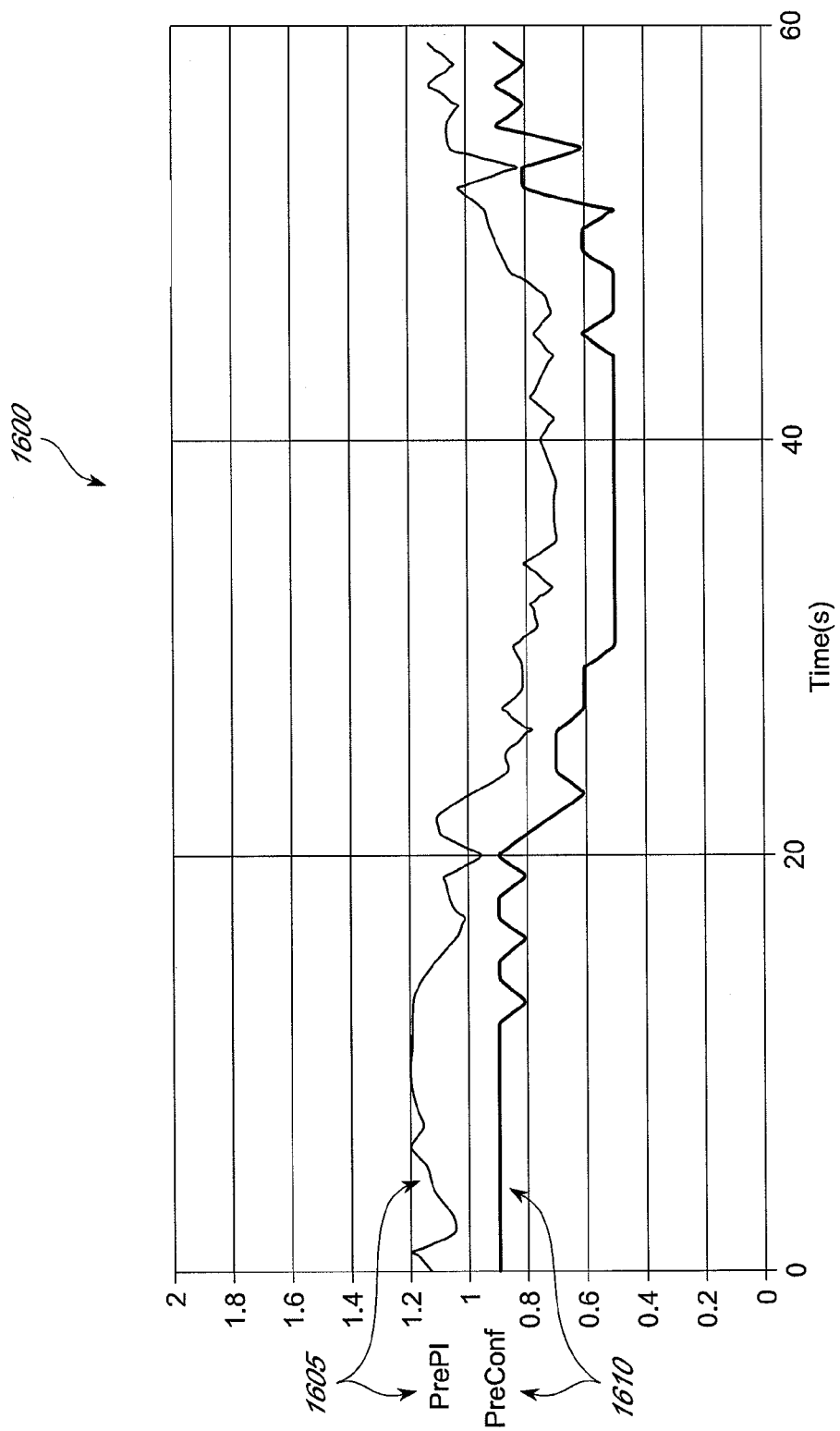
FIG. 16 illustrates an example plot of pre-ductal perfusion index and confidence measurement in a CCHD screen process, according to an embodiment of the present disclosure.

Referring back to FIG. 3C and box 366, in an embodiment, a process or processes executing on one or more signal processors (such as signal processor 326) seek to reduce errors introduced by, for example, the time differential in measurements in the single sensor implementation of CCHD screening processes. In an embodiment, confidence thresholds may indicate when signal quality is sufficiently high to use measurement data. Confidence information may also be used to weight data as it is combined for comparisons. Confidence information may be assigned to windows of data and may be used to reduce an impact of a particular window on a measurement value or adjust the value itself. Such confidence information may be advantageously incorporated into a visual queue, such as a number or a graphic, indicating a confidence in the measurement or screening itself. An embodiment of a confidence measurement is displayed in FIG. 16. FIG. 16 shows an example plot 1600 of a pre-ductal PI graph 1605 and a pre-ductal confidence graph 1610, each versus time (in seconds). The pre-ductal PI graph 1605 will be described below. Pre-ductal confidence is indicated by pre-ductal confidence graph 1610, which varies over time based on, for example, signal quality from the sensor 304 and/or PI measurements as shown in the pre-ductal PI graph 1605. In an embodiment, a sufficiently low confidence level (and/or threshold) results in a measurement error, and no result is reported to the user/caregiver. For example, a confidence threshold may be (on a scale of 0 to 1) 0.5, 0.6, 0.7, 0.8, 0.85, 0.9, 0.95, 0.96, 0.97, 0.98, 0.99, and/or 1, among other possibilities.

Referring back to box 366 in FIG. 3C, additional processing may be accomplished to ensure the measured data is reliable, and/or the user/caregiver may be notified of possible problems with the gathered data. Alternatively, the gathered data may be processed after it is gathered. For example, the sensor data at site one may be gathered and processed, followed by the gathering and processing of the sensor data of site two.

In an embodiment, indications of motion may advantageously cause an audio/visual message to be presented to a caregiver to calm the patient before measurements can be used. In an embodiment, a minimum wait time may ensure that actual stabilization of the data occurs, such as for example, about ten (10) to twenty (20) seconds or more may need to pass after an indication of cessation of motion in the patient.

Figure 15:
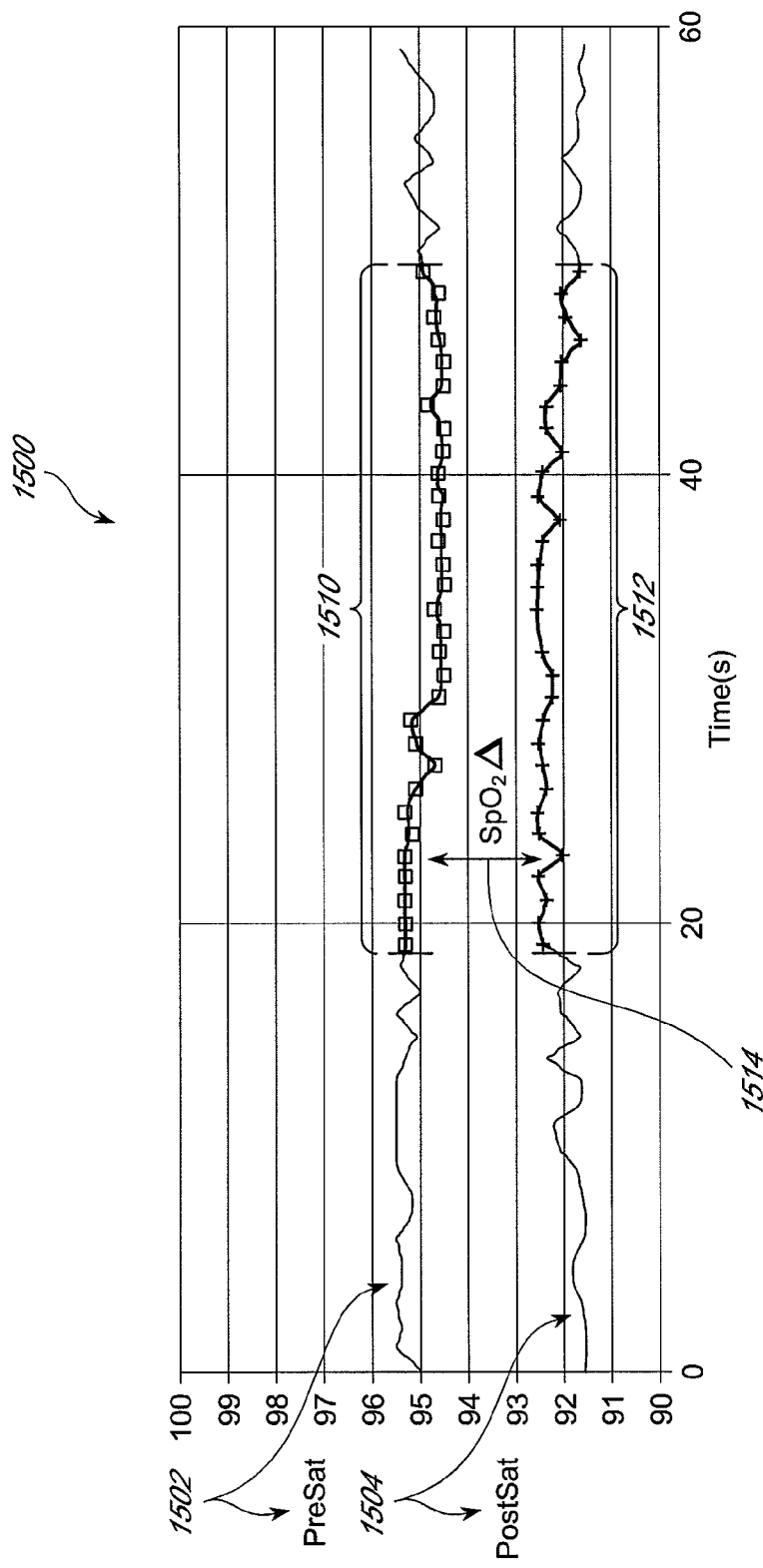
FIG. 15 illustrates an example plot of pre- and post-ductal $SpO_2$ measurements in a CCHD screen process, according to an embodiment of the present disclosure.

In an embodiment, the features of the plethsmographic data or of the oxygen saturation data values can be analyzed to determine when to use measurement data. In the case of the plethsmographic data, determination of how well the waveform fits a model may guide confidence measurements or indicate signal noise. With saturation data, troughs and peaks, and their respective severities may be determined so that measurements for each site are chosen during similar or the same waveform feature, such as, for example, using measurements that correspond to peaks for each site. In an embodiment, the natural high and low cycles of oxygen saturation are used to correlate the measurements. For example, typical pre- and post-ductal $SpO_2$ measurements are illustrated in FIG. 15. FIG. 15 shows an example plot 1500, including a pre-ductal $SpO_2$ graph 1502 and a post-ductal $SpO_2$ graph 1504, each versus time (in seconds). The $SpO_2$ measurements vary cyclically over time. Thus, in order to compare measurements from two different sites taken at different times, the natural cycles of variance in the $SpO_2$ are used to correlate the measurement data. In the example of FIG. 15, a 60 second window of data is taken of both the pre- and post-ductal measurement. The data is time adjusted so that the natural cycles of the $SpO_2$ measurements occur at roughly the same time. A window or timeframe, for example, a 30 second window of time, is analyzed, indicated as 1510 and 1512, respectively, in FIG. 15. This window or timeframe is then used to determine the $SpO_2$ delta 1514. As a result of correlating the pre- and post-ductal $SpO_2$ measurements using the natural cycles, a more accurate delta can be determined.

Referring back to box 366 in FIG. 3C, in an embodiment, additional processing may be performed and/or intermediate data may be accessed to assist in determining which measurements to select for screening deltas. For example, often sophisticated filters are used to smooth saturation measurements. In an embodiment, pre-filtered results may provide more accurate or immediate information on measurement selection. Similarly, ratio or other information may be used in addition to or in place of focusing on oxygen saturation values.

In an embodiment, phases in the respiration cycle may be accounted for to select measurement data. For example, measurement values may correspond to only data during, for example, the inspiration phase, or the like. In an embodiment, respiration or pulse rates may qualify or disqualify measurement data, based on, for example, rate stability or the like.

Other parameter information may also be used. For example, perfusion index ("PI") information may provide indicators on when to select measurement data. In an embodiment, PI may vary for reasons unrelated to CCHD and therefore can be used in certain implementations, such as ranges that qualify or disqualify measurement data or the like. For example, the perfusion index may indicate that signal quality is sufficiently high to use measurement data. A PI measurement is also illustrated in FIG. 16 as pre-ductal PI graph 1605. Although both confidence and PI have been illustrated with respect to a pre-ductal measurement in FIG. 16, it is to be understood that a similar PI and confidence measure may also be determined for a post-ductal measurement.

In box 368 of FIG. 3C, the pulse oximeter 300 may optionally communicate with a remote data processing center, through, for example, the network interface 336. As described below in reference to FIG. 5, current measurement data may be transmitted to the remote data processing center, and/or previous measurement data may be accessed from the remote data processing center, among other things. Thus, the results of multiple measurements may be stored, retrieved, and/or compared as part of the CCHD screening process. Alternatively, measurement data may be stored at the pulse oximeter 300. In an embodiment, the data processing of box 366 takes place at the remote data processing center.

In box 370, the results of the CCHD screening are reported to the caregiver/patient/user. This may be accomplished, for example, by displaying the results on the display 302 as a number, color, and/or other symbol, and/or aurally in the form of, for example, an alarm.

An artisan will recognize from the disclosure herein a wide variety of indicators or combinations of indicators for determining when to select measurement data for use in CCHD screening processes. For example, segments or whole windows of data for the various parameters and indicators discussed in the foregoing may be combined to provide additional insight into measurement selection. Moreover, any or combinations of the foregoing may be used to adjust a particular measurement instead of seeking a different measurement.

FIG. 4 illustrates an embodiment of the CCHD screening system incorporating dual (or stereo) sensors. FIG. 4 includes a pulse oximeter 400, a signal processing device 406, a first sensor 408, and a second sensor 409. Further, the pulse oximeter 400 includes a display 402, a communication port 403, and a portable oximeter 404. Such a pulse oximeter is commercially available from Masimo Corporation of Irvine, Calif. Other CCHD systems may employ more than two sensors. In an embodiment, the pulse oximeter 400 includes a USB or other communication port 403 that connects to the signal processing device 406. In this embodiment, each of the dual sensors (first sensor 408 and second sensor 409) connects to the signal processing device 406. Either of the first sensor 408 or the second sensor 409, or both the first sensor 408 and the second sensor 409, may comprise any combination of disposable, reusable, and/or resposable sensors. As described above, the first sensor 408 and/or the second sensor 409 may be configured for use with an infant. Additionally, the two sensors are not required to be of the same type, but may be any combination of suitable sensors. For example, in some embodiments, the first sensor 408 and/or the second sensor 409 may include finger, toe, or ear sensors, or any combination of finger, toe, or ear sensors. In another example, the first sensor 408 and/or the second sensor 409 may be a wrist-type sensor configured to surround the wrist or ankle of an infant. The signal processing device 406 provides stereo processing of sensor signals, such as those disclosed in the '065 patent. In an embodiment, such processing may include separate oximeter calculators logically similar to having two independent oximeters, one for each sensor. The pulse oximeter 400 may include components similar to those of the pulse oximeter 300 of FIG. 3B. Specifically, the pulse oximeter 400 may include a signal processor, among other things. Processing of sensor data may take place in the pulse oximeter 400 and/or the signal processing device 406.

In this stereo embodiment of two (2) or more sensors, while there may not necessarily be time differentials between measurements, the data from each sensor may be of varying quality. Thus, many of the same procedures disclosed in the foregoing will apply. For example, at a particular time, the data from the baseline sensor may be clean with a high confidence while the data from the alternate sensor may have low quality from motion artifact, such as, for example, an infant kicking but not moving their right hand. Thus, the signal processing device 406 may use the foregoing processes to select measurement values from each sensor at different times. In such cases, determining which measurements should be used involves determinations similar to those used in the single sensor implementation. Alternatively, the signal processing device 406 may wait and select a time when both sensors produce usable measurement data, similar data conditions, or the like.

In an embodiment, the signal processing device 406 determines measurements for each of first sensor 408 and second sensor 409, and forwards measurement values to the pulse oximeter 400. The monitor 400 advantageously includes CCHD screening modules that guide a caregiver through the screening process. In other embodiments, the signal processing device 406 executes the screening and sends flags or messages to the display 402 and/or the portable oximeter 404 directing the display 402 and/or the portable oximeter 404 to display caregiver instructions and/or output results.

Although disclosed as the processing device 406 separate from the pulse oximeter 400, an artisan will recognize from the disclosure herein that the processing of the signal processing device 406 may be incorporated into the pulse oximeter 400 and/or the portable oximeter 404.

Figure 5:
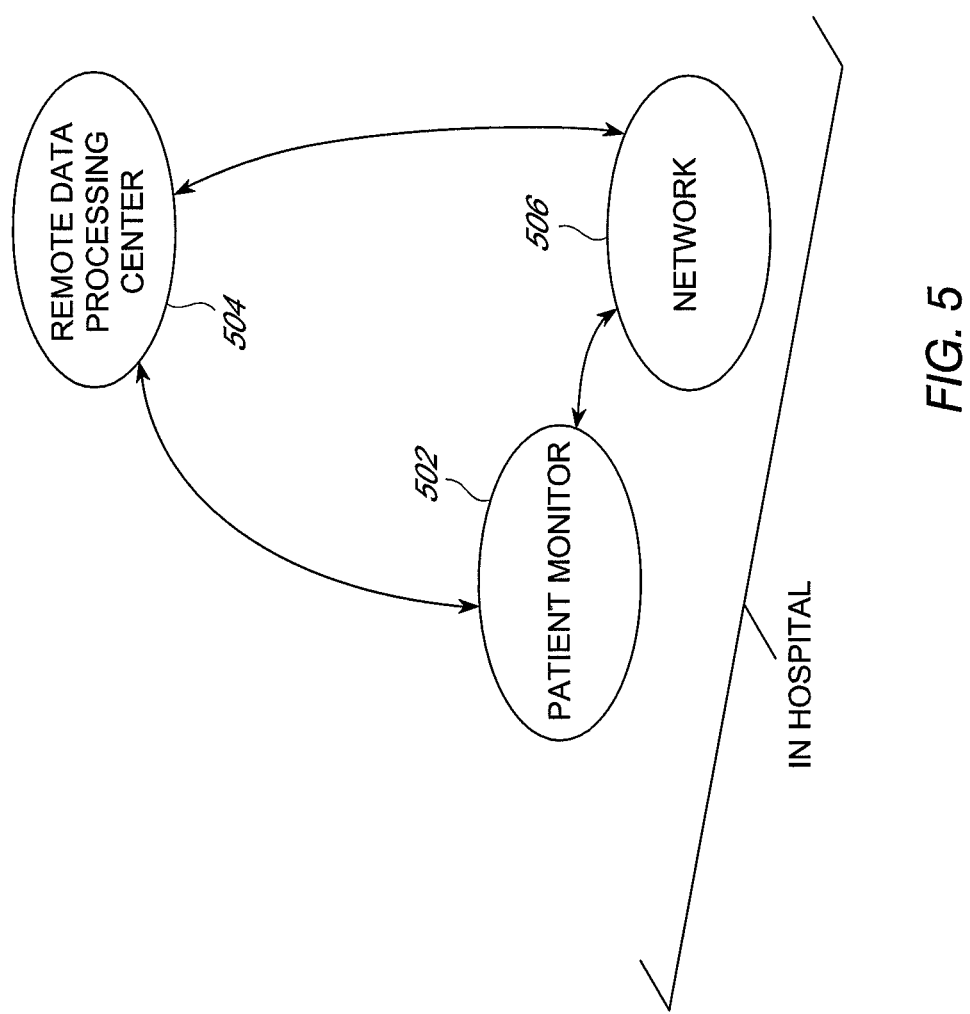
FIG. 5 illustrates a data diagram of a data sharing system, according to an embodiment of present disclosure.

FIG. 5 illustrates a data diagram of a data sharing system, according to an embodiment of present disclosure. FIG. 5 includes a patient monitor 502, a remote data processing center 504, and a network 506. In an embodiment, the patient monitor 502 may include, for example, either the pulse oximeter 300 of FIG. 3A or the pulse oximeter 400 of FIG. 4. In an embodiment, the patient monitor 502 and the network 506 may communicate with one another, and may be located in a hospital, while both the patient monitor 502 and the network 506 may advantageously communicate with the remote data processing center 504. The network 506 may include, for example, Masimo's Patient SafetyNet System, a hospital patient data system, and/or any other wired or wirelessly connected system. An artisan will recognize that communications among any of the patient monitor 502, the remote data processing center 504, and the network 506 may be through any appropriate wired and/or wireless data transmission, and may use any suitable communications protocol. For example, communication may be serial or parallel, through Universal Serial Bus (USB) (wired or wireless), Ethernet, Bluetooth, Near Field Communications (NFC), radio frequency (RF), infrared, and/or WiFi (such as any 802.1x interface), among others as is known in the art.

In an embodiment, the remote data processing center 504 may store, for example, Patient ID's, device information (such as, for example, patient monitor 502 device information), sensor information, measurement data, screening data, and/or screening determinations for comparisons with later screening events. For example, the CCHD screening process of FIG. 2 includes multiple repeat screens. In this example, previous screening data for a particular patient, among other things, may be requested by the patient monitor 502, when for example, a new screening is performed. Thus, the data from the two screening may be compared or used in some other way. Such communication may advantageously be wirelessly directed from the patient monitor 502 to the remote data processing center 504, or through one or more intermediary networks (such as the network 506). For example, the patient monitor 502 may include wireless communication to a hospital or other network which eventually communicates with the remote data processing center 504.

In an embodiment, the pulse oximeter 300 may communicate with network 506 (or other host digital network or system) to store or upload measurement data associated with a unique identifier to remote data processing center 504. The network 506 may include multiple networks or systems. The pulse oximeter 300 may access previously stored information, such as, for example, earlier screening data stored at the remote data processing center 504 of a remote network, to complete or increment the CCHD screening process. In an embodiment, a first network may be an institutional network such as a hospital data system, a cellular or other data system, or the like, wirelessly communicating with the pulse oximeter 300 or monitor. The system or systems eventually allow communication to a remote data processing center 504 or other processing center that stores the measurement information in a manner that provides for retrieval and appropriate association with newly acquired data.

As will be described in detail below, FIGS. 6-9, 10A-B, 11A-B, 12A-C, 13A-C, and 14A-D illustrate example screen shots and/or displays of a pulse oximeter monitor (such as the pulse oximeter 300 of FIG. 3A or the pulse oximeter 400 of FIG. 4) and/or other CCHD measurement device configured for measuring CCHD, according to embodiments of the present disclosure.

Figure 6:
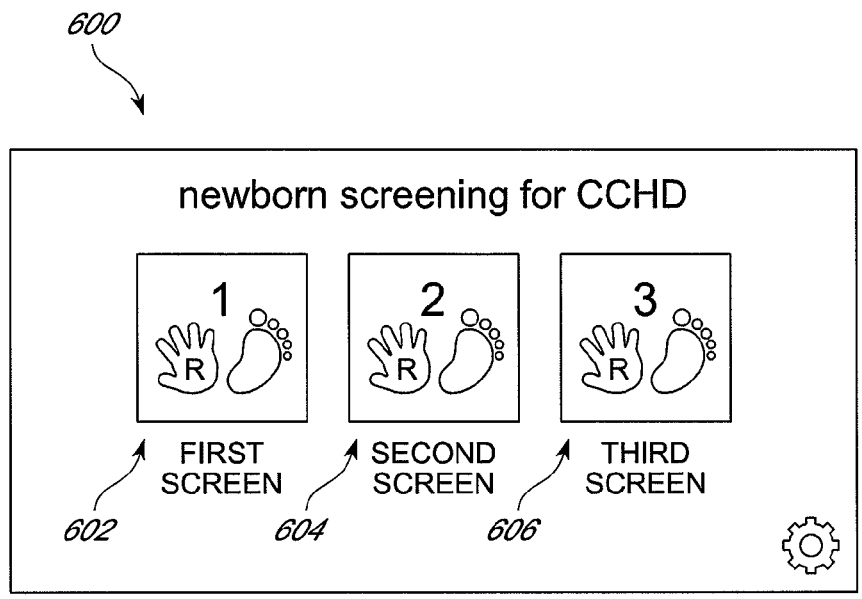
FIG. 6 illustrates an example screen shot of a pulse oximeter monitor configured for measuring CCHD, according to an embodiment of the present disclosure.

FIG. 6 illustrates a screen shot 600 of a pulse oximeter monitor configured for measuring CCHD. The screen shot 600 includes a first screen 602, second screen 604, and third screen 606 for measuring CCHD. These three screens correlate to the three separate measurement recommendations for measuring CCHD, as described in reference to FIG. 2. A touch screen can be provided in the pulse oximeter monitor so that a caregiver need only touch each measurement (for example, first screen 602, second screen 604, and third screen 606) in succession to begin the three different measurement processes.

Figure 7:
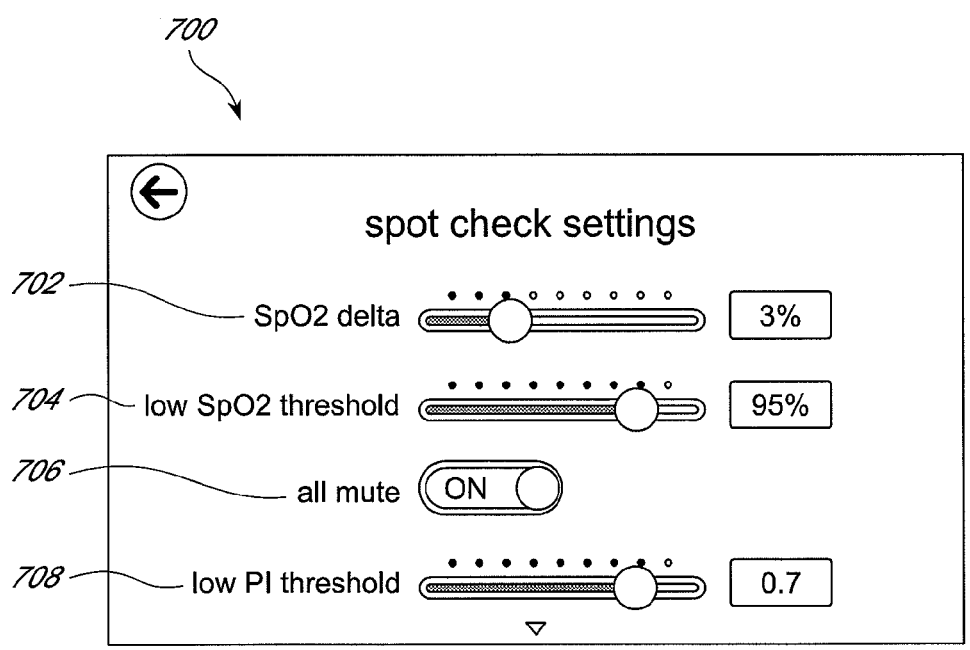
FIG. 7 illustrates an example screen shot, including spot check settings, of a pulse oximeter monitor configured for measuring CCHD, according to an embodiment of the present disclosure.

FIG. 7 illustrates various spot check settings that are available on the pulse oximeter monitor and/or CCHD measurement device of the present disclosure. A SpO$_2$ delta 702 allows a caregiver to dictate a specific difference in SpO$_2$ between measurement sites that will indicate a CCHD problem. The value can range between 1 and 10 with a default value of 3. The low SpO$_2$ threshold 704 indicates a minimal passing SpO$_2$ value for a test result. The value can range between 85-100 with a default value of 95. The all mute 706 mutes all noise from the pulse oximeter monitor and/or CCHD measurement device. The low PI threshold 708 indicates a minimum PI measurement value that may still indicate a valid test result. This value can range between 0.1 and 1 with a default value of 0.7.

Figure 8:
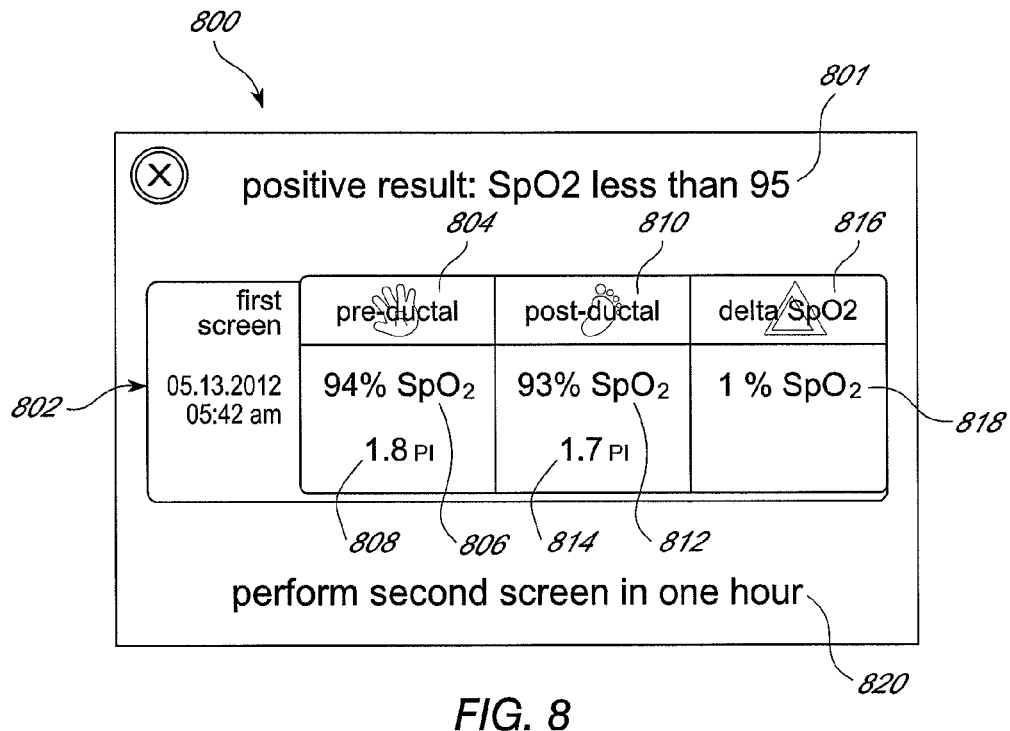
FIGS. 8-9 illustrate example screen shots, including test results, of a pulse oximeter monitor configured for measuring CCHD, according to an embodiment of the present disclosure.

FIG. 8 illustrates a display of a first test results page 800. The first test results page 800 includes a first test results indication 801. In the embodiment of first test results page 800, a positive result was obtained, but it was at a saturation value of less than 95%. The first test results page 800 also includes the time of the test 802, the pre-ductal results 804 and post-ductal results 810, including the respective SpO$_2$ values 806, 812 and PI values 808 and 814, as well as the delta SpO$_2$ 816 illustrating the delta SpO$_2$ value 818. The first test results page 800 also includes a next step indication 820. For example, in the embodiment of FIG. 8, the next step may indicate that a second screen test is to be performed in an hour. Alternatively, the next step may indicate that no further testing is required (in the event of, for example, a negative screen).

Figure 9:
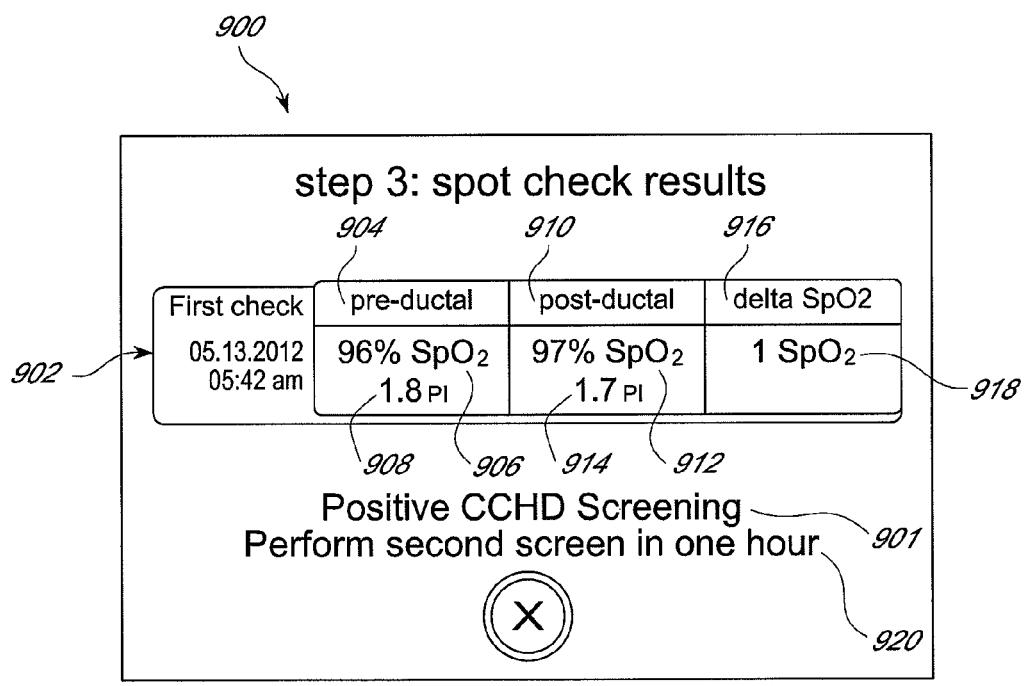

FIG. 9 illustrates another example of a first test results page 900. The test results page has similar features corresponding to that of FIG. 8 shown in an alternative format. The first test results page 900 includes a first test results indication 901. In the embodiment of first test results page 900, a positive result was obtained. The first test results page 900 also includes the time of the test 902, the pre-ductal results 904 and post-ductal results 910, including the respective SpO$_2$ values 906, 912 and PI values 908 and 914, as well as the delta SpO$_2$ 916 illustrating the delta SpO$_2$ value 918. The first test results page 900 also includes a next step indication 920.

Figure 10A:
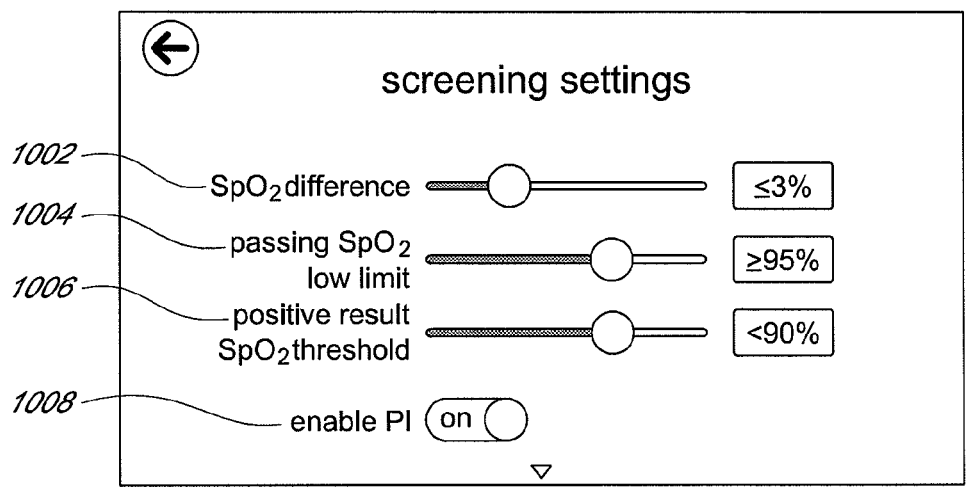
FIGS. 10A-B illustrate example screen shots, including alternative screening settings, of a pulse oximeter monitor configured for measuring CCHD, according to an embodiment of the present disclosure.
Figure 10B:
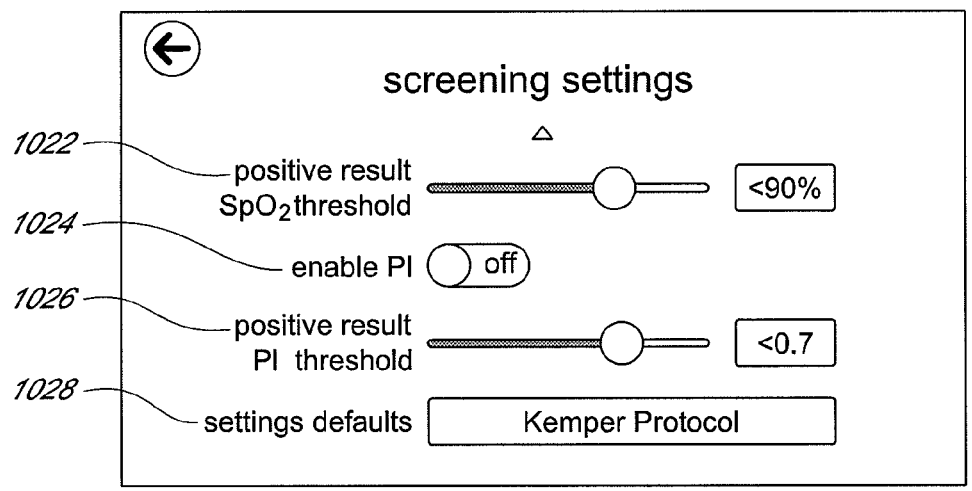

FIGS. 10A and 10B illustrate additional alternative embodiments of settings available for the CCHD monitor of the present disclosure. Referring to FIG. 10A, screen 1000 includes settings which indicate the difference in SpO$_2$ readings (SpO$_2$ difference 1002) between sites to indicate a CCHD problem. The screen settings also include passing SpO$_2$ low limit 1004, positive result SpO$_2$ threshold 1006, and enable PI 1008. Referring to FIG. 10B, additional settings on screen 1020 include positive result SpO$_2$ threshold 1022, enable PI 1024, positive result PI threshold 1026, and settings defaults 1028. The settings defaults can include different protocols for measuring CCHD including the Kemper Protocol.

Figure 11A:
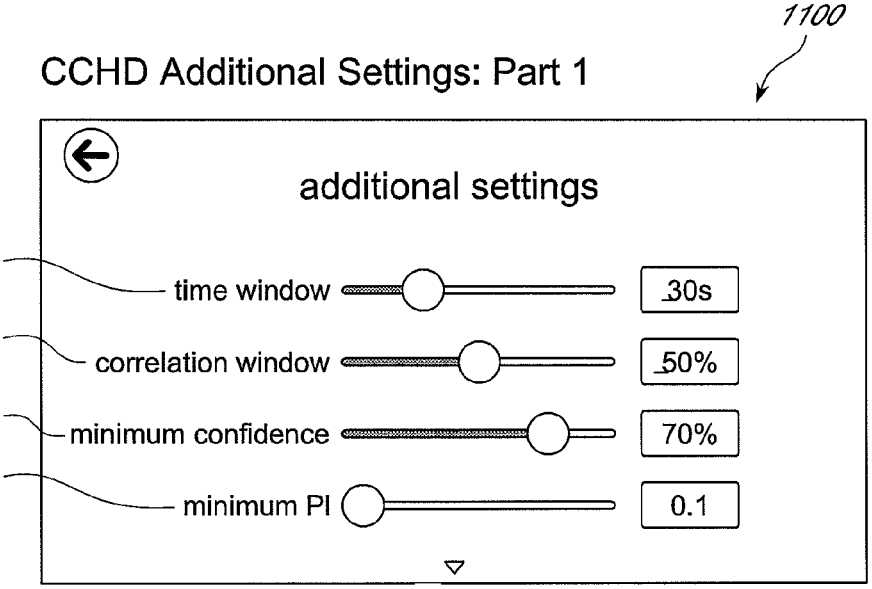
FIGS. 11A-B illustrate example screen shots, including additional settings, of a pulse oximeter monitor configured for measuring CCHD, according to an embodiment of the present disclosure.
Figure 11B:
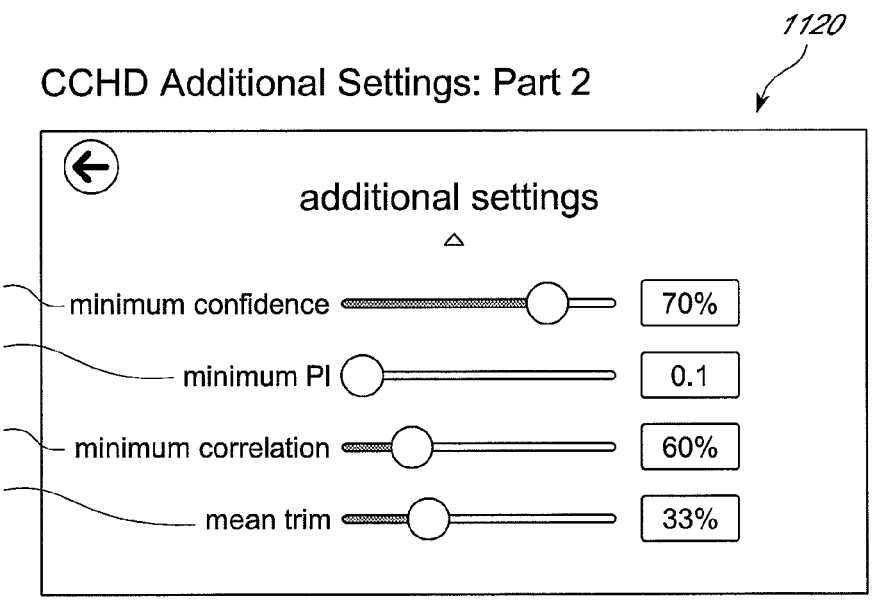

FIG. 11A illustrates additional advanced settings in screen 1100, including a time window 1102, a correlation window 1104, a minimum confidence 1106, and minimum PI 1108. In FIG. 11B other settings are illustrated in screen 1120, including minimum confidence 1122, minimum PI 1124, minimum correlation 1126, and mean trim 1128.

Figure 12A:
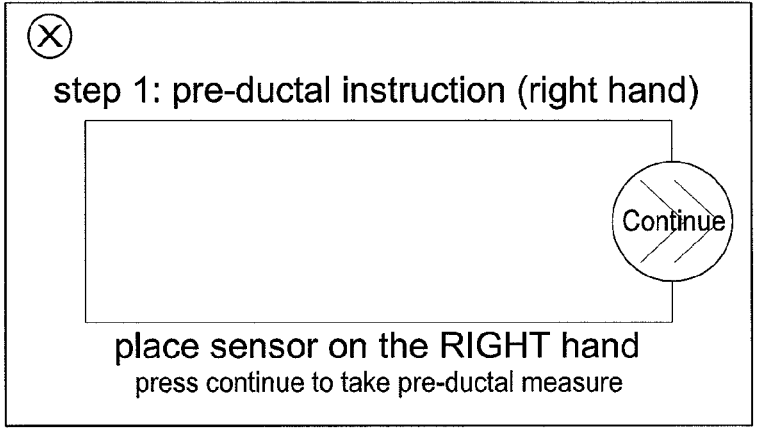
Figure 12B:
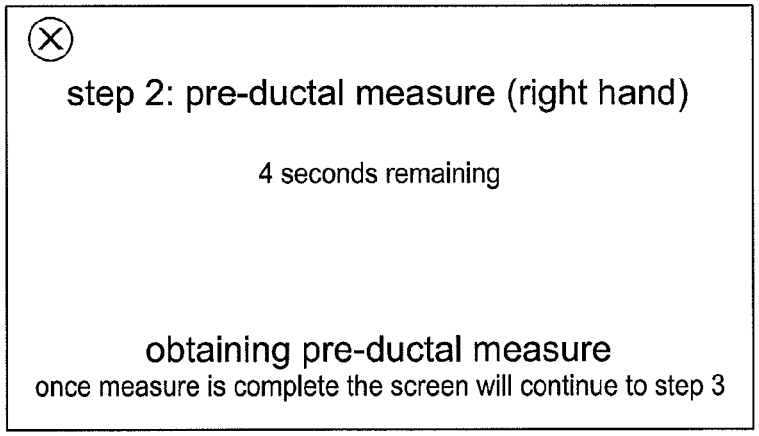
Figure 12C:
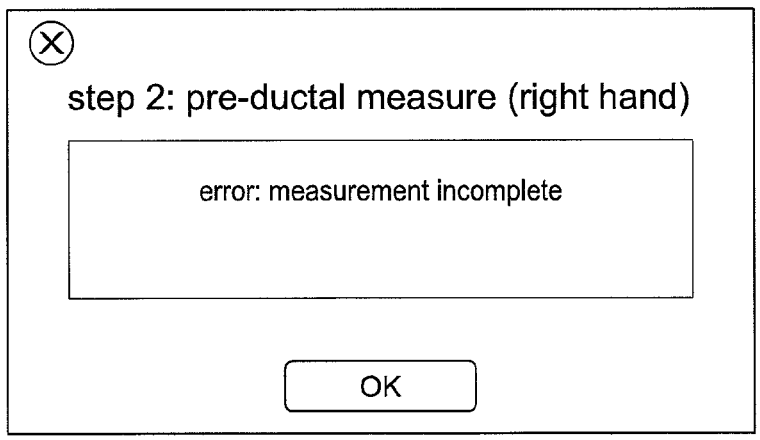

Once all of the settings are configured, the CCHD screening device of the present disclosure provides step by step instructions for performing a CCHD test protocol. FIGS. 12A-C, 13A-C, and 14A-D illustrate instructions provided for the single sensor CCHD monitor of the present disclosure. FIGS. 12A-C illustrate an embodiment of various protocol step-by-step instructions. For the pre-ductal measurement, instruction screen 1200 instructs a caregiver to place the sensor on the right hand and press a button on the screen to move to the next instruction screen 1220. Instruction screen 1220 indicates that a measurement is taking place. If an error occurs in the measurement, an error screen 1240 is displayed. In an embodiment, the CCHD screening system (including, for example, pulse oximeter 300 or pulse oximeter 400) controls and tracks the implementation of the screening process, including instructions to caregivers on next steps, as described. Additional examples of instruction may include "Attach Sensor to Right Hand," "Attach Sensor to Alternate Site," "Attach Sensor to Right Foot," "Attach Sensor to Left Foot," "Calm Patient," "Adjust Sensor Positioning," or the like.

Figure 13A:
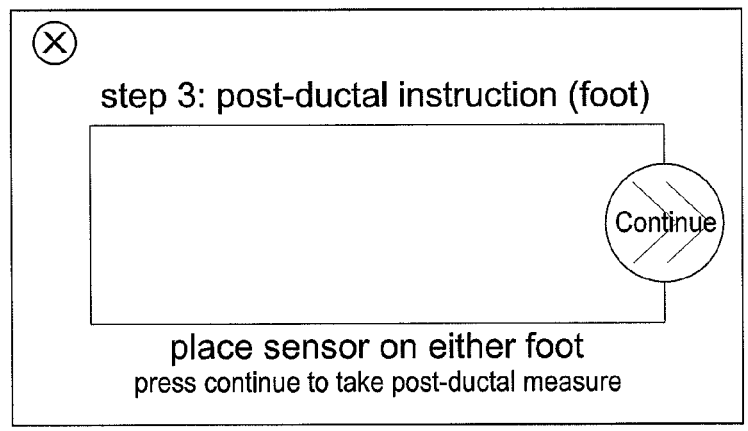
Figure 13B:
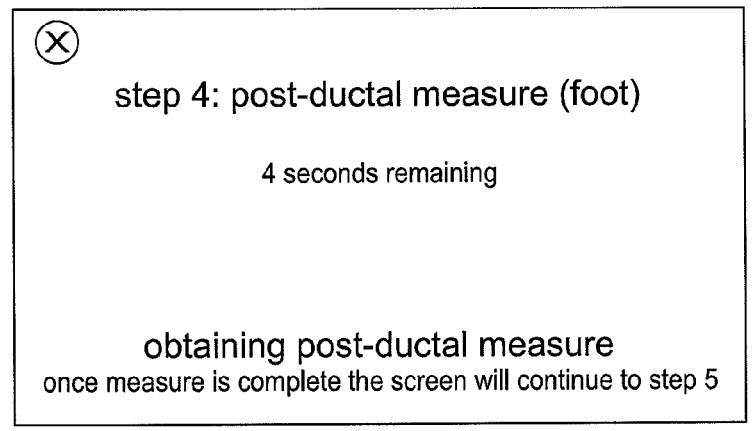
Figure 13C:
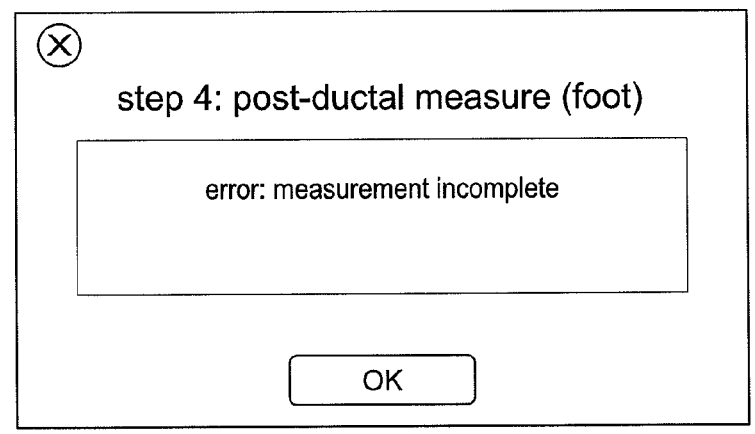

Once the pre-ductal measurement is obtained, the instructions move on to the instruction screens of FIGS. 13A-C. Instruction screen 1300, labeled as step 3, instructs the caregiver to place the sensor on the either foot of the patient and press a button to continue to instruction screen 1320. In instruction screen 1320, labeled as step 4, the post-ductal measurement is obtained. If an error occurs in the post-ductal measurement, an error screen 1340 is presented to the user.

The instructions continue with FIGS. 14A-D. Once the post-ductal measurement is obtained, results screen 1400, labeled as step 5, is displayed. The results screen 1400 provides the pre- and post-ductal screening results, as well as the difference in SpO$_2$. The results screen 1400 illustrates an embodiment in which a passing test was obtained and instructions that the test was passed are provided on the screen at 1405. Alternatively, if a potential problem was found, as illustrated in results screen 1420 of FIG. 14B, then an instruction is provided at 1425 instructing the care giver to perform a second test in one hour. If a second screening indicates a failing test, as illustrated in results screen 1440 of FIG. 14C, then an instruction is provided to perform a third screen testing in one hour at 1445. If the results of the third test also indicate a problem, for example in screen 1460 of FIG. 14D, then an instruction is provided to refer the newborn for further medical evaluation at 1465. As described above, the CCHD screening system may include a quality indicator providing information on the confidence in the screening measurements. A quality measure may be included for each measurement, for the entire screen, or the like. For example, the display may indicate "Positive Screen, 72% Confidence." In an embodiment, a minimum confidence threshold may be used to instruct a caregiver to repeat the measurements and/or restart the screening process. Moreover, the oximeter may produce an audio/visual alarm indicating time for a repeat screen, may accept patient information including a patient identifier, and the like.

Although the foregoing has been described in terms of certain preferred embodiments, other embodiments will be apparent to those of ordinary skill in the art from the disclosure herein. For example, other CCHD screening methodologies may take advantage of the processes for matching measurements disclosed herein. Moreover, data conditions from one screen may influence when measurements are chosen for subsequent screens. For example, if choosing according to peaks in the $SpO_2$ values was implemented to match measurement conditions in one screen, the same may be used or implemented in subsequent screens. Accordingly, the present disclosure is not intended to be limited by the reaction of the preferred embodiments, but is to be defined by reference to the appended claims.

In addition to the foregoing, all publications, patents, and patent applications mentioned in this specification are herein incorporated by reference to the same extent as if each individual publication, patent, or patent application was specifically and individually indicated to be incorporated by reference.

Moreover, the oximeters discussed in the foregoing may include many or all of the features of basic pulse oximeters that determine measurements for blood oxygen saturation ("$SpO_2$"), pulse rate ("PR") and plethysmographic information, to read-through-motion oximeters, to co-oximeters that determine measurements of many constituents of circulating blood. For example, Masimo Corporation of Irvine Calif. ("Masimo") manufactures pulse oximetry systems including Masimo SET® low noise optical sensors and read through motion pulse oximetry monitors for measuring $SpO_2$, PR, perfusion index ("PI") and others. Masimo sensors include any of LNOP®, LNCS®, SoftTouch™ and Blue™ adhesive or reusable sensors. Masimo oximetry monitors include any of Rad-8®, Rad-5®, Rad-5v® or SatShare® monitors.

Also, many innovations improving the measurement of blood constituents are described in at least U.S. Pat. Nos. 6,770,028; 6,658,276; 6,157,850; 6,002,952; 5,769,785 and 5,758,644, and are incorporated by reference herein. Corresponding low noise optical sensors are disclosed in at least U.S. Pat. Nos. 6,985,764; 6,813,511; 6,792,300; 6,256,523; 6,088,607; 5,782,757 and 5,638,818, and are incorporated by reference herein.

Masimo also manufactures more advanced co-oximeters including Masimo Rainbow® SET, which provides measurements in addition to $SpO_2$, such as total hemoglobin (SpHb™), oxygen content (SpCO™), methemoglobin (SpMet®), carboxyhemoglobin (SpCO®) and PVI®. Advanced blood parameter sensors include Masimo Rainbow® adhesive, ReSposable™ and reusable sensors. Masimo's advanced blood parameter monitors include Masimo Radical-7™, Rad-87™, and Rad-57™ monitors as well as Pronto and Pronto-7 spot check monitors.

Innovations relating to these more advanced blood parameter measurement systems are described in at least U.S. Pat. Nos. 7,647,083; 7,729,733; U.S. Pat. Pub. Nos. 2006/0211925; and 2006/0238358, incorporated by reference herein.

Such advanced pulse oximeters, low noise sensors and advanced blood parameter systems have gained rapid acceptance in a wide variety of medical applications, including surgical wards, intensive care and neonatal units, general wards, home care, physical training, and virtually all types of monitoring scenarios.

Thus, by employing the embodiments of the CCHD screening processes and systems disclosed herein, CCHD, particularly PDA, may be more accurately detected and diagnosed. Specifically, false positives may be reduced, variances in $SpO_2$ may be detected and filtered, caregivers may be more properly directed, and/or measurement confidence may be evaluated, among other advantages.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

While certain embodiments of the inventions disclosed herein have been described, these embodiments have been presented by way of example only, and are not intended to limit the scope of the inventions disclosed herein. Indeed, the novel methods and systems described herein can be embodied in a variety of other forms; furthermore, various omissions, substitutions and changes in the form of the methods and systems described herein can be made without departing from the spirit of the inventions disclosed herein. The claims and their equivalents are intended to cover such forms or modifications as would fall within the scope and spirit of certain of the inventions disclosed herein.

What is claimed is:

1. A method of detecting a critical congenital heart defect using a pulse oximeter, the method comprising:

instructing a caregiver, using a display of a pulse oximeter, to position a noninvasive sensor to a first measurement site predetermined to be indicative of a pre-ductal blood oxygenation level, wherein said noninvasive sensor is configured to output signals responsive to attenuation of light at measurement sites on a patient, and wherein said pulse oximeter is in communication with the noninvasive sensor to drive light sources of said noninvasive sensor and receive said output signals;

receiving, during a first duration of time, said output signals to obtain a first waveform responsive to a pre-ductal oxygen saturation of the patient, said first duration of time corresponding to when said noninvasive sensor is positioned at said first measurement site;

instructing the caregiver, using the display of the pulse oximeter, to position said noninvasive sensor to a second measurement site predetermined to be indicative of a post-ductal blood oxygenation level;

receiving, during a second duration of time, said output signals to obtain a second waveform responsive to a post-ductal oxygen saturation of the patient, said second duration of time corresponding to when said noninvasive sensor is positioned at said second measurement site;

electronically determining, by one or more signal processors, one or more waveform features in said first waveform responsive to said pre-ductal oxygen saturation;

electronically determining, by the one or more signal processors, one or more of said one or more waveform features in said second waveform responsive to said post-ductal oxygen saturation;

electronically time-wise aligning, by the one or more signal processors, one or more of said one or more waveform features from said first waveform with one or more of said one or more waveform features from said second waveform;

electronically determining, by the one or more signal processors, a pre-ductal value of said first waveform at a first time;

electronically determining, by the one or more signal processors, a post-ductal value of said second waveform at said first time taking into account said time-wise aligning; and in response to determining said pre-ductal value and said post-ductal value differ by a predetermined threshold, outputting display indicia to said display indicating a likelihood that said patient has said critical congenital heart defect.

2. The method of claim 1, wherein said first time comprises a third duration of time, and wherein determining said pre-ductal value and said post-ductal value differ by the predetermined threshold comprises:

calculating an average difference between said pre-ductal value and said post-ductal value over the third duration of time.

3. The method of claim 2, wherein said first duration of time and said second duration of time each comprise at least sixty seconds.

4. The method of claim 3, wherein said third duration of time comprises at least thirty seconds.

5. The method of claim 1, wherein said one or more waveform features from said first waveform comprise at least one of: a trough, a peak, a natural high cycle of oxygen saturation, a natural low cycle of oxygen saturation, or a cyclical variation.

6. The method of claim 1 further comprising:

discarding a waveform when a quality of said output signals is outside of a pre-determined range.

7. The method of claim 1 further comprising:

receiving said signal outputs to obtain a third waveform responsive to a blood perfusion level of the patient, wherein a waveform discarded when the blood perfusion level associated with the waveform is outside of a pre-determined range.

8. A pulse oximetry based system configured to detect a critical congenital heart defect, the system comprising:

a noninvasive sensor configured to output signals responsive to an attenuation of light at measurement sites on a patient; and a pulse oximeter in communication with the noninvasive sensor to drive light sources of said noninvasive sensor and to receive said output signals, said pulse oximeter including one or more signal processors, the signal processors configured to:

instruct a caregiver, using a display of the pulse oximeter, to position said noninvasive sensor to a first measurement site predetermined to be indicative of a pre-ductal blood oxygenation level;

receive, during a first duration of time, said output signals to obtain a first waveform responsive to a pre-ductal oxygen saturation of the patient, said first duration of time corresponding to when said noninvasive sensor is positioned at said first measurement site;

instruct the caregiver, using the display of the pulse oximeter, to position said noninvasive sensor to a second measurement site predetermined to be indicative of a post-ductal blood oxygenation level;

receive, during a second duration of time, said output signals to obtain a second waveform responsive to a post-ductal oxygen saturation of the patient, said second duration of time corresponding to when said noninvasive sensor is positioned at said second measurement site;

electronically determine one or more waveform features in said first waveform responsive to said pre-ductal oxygen saturation;

electronically determine one or more of said one or more waveform features in said second waveform responsive to said post-ductal oxygen saturation;

electronically time-wise align one or more of said one or more waveform features from said first waveform with one or more of said one or more waveform features from said second waveform;

electronically determine a pre-ductal value of said first waveform at a first time;

electronically determine a post-ductal value of said second waveform at said first time taking into account said time-wise aligning; and in response to determining said pre-ductal value and said post-ductal value differ by a predetermined threshold, output display indicia to said display indicating a likelihood that said patient has said critical congenital heart defect.

9. The system of claim 8, wherein said first time comprises a third duration of time, and wherein determining said pre-ductal value and said post-ductal value differ by the predetermined threshold comprises:

calculating an average difference between said pre-ductal value and said post-ductal value over the third duration of time.

10. The system of claim 9, wherein said first duration of time and said second duration of time each comprise at least sixty seconds.

11. The system of claim 10, wherein said third duration of time comprises at least thirty seconds.

12. The system of claim 8, wherein said one or more waveform features from said first waveform comprise at least one of: a trough, a peak, a natural high cycle of oxygen saturation, a natural low cycle of oxygen saturation, or a cyclical variation.

13. The system of claim 8, wherein the signal processors are further configured to:

discard a waveform when a quality of said output signals is outside of a pre-determined range.

14. The system of claim 8, wherein the signal processors are further configured to:
  receive said signal outputs to obtain a third waveform responsive to a blood perfusion level of the patient; and
  discard a waveform when the blood perfusion level associated with the waveform is outside of a pre-determined range.

\* \* \* \* \*